(12) United States Patent
Benner

(10) Patent No.: US 7,666,851 B1
(45) Date of Patent: Feb. 23, 2010

(54) THREE RING FUSED ANALOGS OF ISOGUANOSINE

(76) Inventor: Steven Albert Benner, 1501 NW. 68th Ter., Gainesville, FL (US) 32605-4147

(*) Notice: Subject to any disclaimer, the term of this patent is extended or adjusted under 35 U.S.C. 154(b) by 365 days.

(21) Appl. No.: 11/436,970

(22) Filed: May 18, 2006

(51) Int. Cl.
| | |
|---|---|
| A61K 31/702 | (2006.01) |
| A61K 31/7056 | (2006.01) |
| A61K 31/706 | (2006.01) |
| A61K 31/7115 | (2006.01) |
| C07H 21/02 | (2006.01) |
| C07H 21/04 | (2006.01) |
| C07H 19/23 | (2006.01) |

(52) U.S. Cl. .................. 514/44; 536/23.1; 536/25.3; 536/26.2; 536/26.3; 536/26.6
(58) Field of Classification Search .......... None
See application file for complete search history.

(56) References Cited

U.S. PATENT DOCUMENTS 7,268,119 B2 * 9/2007 Cook et al. .............. 514/43

FOREIGN PATENT DOCUMENTS

WO  WO2004/048376  * 10/2004

* cited by examiner

*Primary Examiner*—Shaojia Anna Jiang
*Assistant Examiner*—Eric S Olson

(57) ABSTRACT

This invention relates to the field of nucleic acid chemistry, more specifically to the field of compositions and processes that are nucleic acid analogs. More specifically, it relates to purine analogs that contain three rings, where the third ring bridges the exocyclic substituent at position 6 to position 7, using the purine numbering system. Still more specifically it relates to analogs having this structure that are able to form nucleobase pairs having the Watson-Crick geometry with a pyrimidine or pyrimidine analog, where the nucleobase pair is joined by hydrogen bonding patterns that either present a standard hydrogen bonding pattern, or a non-standard hydrogen bonding pattern. Most specifically, it to nucleoside analogs that are analogs of isoguanosine, but where the 5-6 ring system of the purine ring in isoguanosine is fused to another five- or six-membered ring, where the fused ring joins the exocyclic amino group with an atom that is, by analogy, at position 7 of the isoguanine ring system. Compositions having this structure can support a base pair with isocytosine joined by three hydrogen bonds, or a base pair with a diaminodiazanaphalene riboside, or 2'-deoxyriboside, or an analog, joined by four hydrogen bonds.

2 Claims, 15 Drawing Sheets

3,5,7-triamino-s-triazolo[4,3-a]-s-triazene (Aldrich)

puDAAD source
WO 2004/048376
pyADDA

THREE RING FUSED ANALOGS OF ISOGUANOSINE

FIELD

This invention relates to the field of nucleic acid chemistry, more specifically to the field of compositions and processes that are nucleic acid analogs. More specifically, it relates to purine analogs that contain three rings, where the third ring bridges the exocyclic substituent at position 6 to position 7, using the purine numbering system. Still more specifically it relates to analogs having this structure that are able to form nucleobase pairs having the Watson-Crick geometry with a pyrimidine or pyrimidine analog, where the nucleobase pair is joined by hydrogen bonding patterns that either present a standard hydrogen bonding pattern, or a non-standard hydrogen bonding pattern. Most specifically, it to nucleoside analogs that are analogs of isoguanosine, but where the 5-6 ring system of the purine ring in isoguanosine is fused to another five- or six-membered ring, where the fused ring joins the exocyclic amino group with an atom that is, by analogy, at position 7 of the isoguanine ring system.

BACKGROUND

Natural oligonucleotides bind to complementary oligonucleotides according to the well-known rules of nucleobase pairing first elaborated by Watson and Crick in 1953, where adenine (A) pairs with thymine (T) (or uracil, U, in RNA), and guanine (G) pairs with cytosine (C), with the complementary strands anti-parallel to one another. In this disclosure, "DNA" or "nucleic acid" is understood to include, as appropriate, both DNA (where the sugar is 2'-deoxyribose) and RNA (where the sugar is ribose), as well as derivatives where the sugar is modified, as in 2'-O-methyl, 2'-O-allyl, 2'-deoxy-2'-fluoro, and 2',3'-dideoxynucleoside derivatives, nucleic acid analogs based on other sugar backbones, such as threose, locked nucleic acid derivatives, bicyclo sugars, or hexose, glycerol and glycol sugars [Zhang, L., Peritz, A., Meggers, E. (2005) A simple glycol nucleic acid. J. Am. Chem. Soc. 127, 4174-4175], nucleic acid analogs based on non-ionic backbones, such as "peptide nucleic acids", these nucleic acids and their analogs in non-linear topologies, including as dendrimers, comb-structures, and nanostructures, and these nucleic acids and their analogs carrying tags (e.g., fluorescent, functionalized, or binding) to the ends, sugars, or nucleobases.

These pairing rules allow for the specific hybridization of an oligonucleotide to a complementary oligonucleotide, making oligonucleotides valuable as probes in the laboratory, in diagnostic applications, as messages that can direct the synthesis of specific proteins, and in a wide range of other applications well known in the art. Such base pairing is used, for example and without limitation, to capture other oligonucleotides to beads, arrays, and other solid supports, to allow nucleic acids to fold in hairpins, beacons, and catalysts, as supports for functionality, such as fluorescence, fluorescence quenching, binding/capture tags, and catalytic functionality, as part of more complex architectures, including dendrimers and nanostructures, and as scaffolds to guide chemical reactions.

Further, nucleobase pairing is the basis by which enzymes are able to catalyze the synthesis of new oligonucleotides that are complementary to template nucleotides. In this synthesis, building blocks (normally the triphosphates of ribo- or deoxyribonucleosides carrying of A, T, U, C, or G) are directed by a template oligonucleotide to form a complementary oligonucleotide with the complementary sequence. This process is the basis for replication of all forms of life, and also serves as the basis for technologies for enzymatic synthesis and amplification of specific heterosequence nucleic acids by enzymes such as DNA and RNA polymerase, in the polymerase chain reaction (PCR), and in a variety of architectures that may involve synthesis, ligation, cleavage, immobilization and release, inter alia, used in technology to detect nucleic acids.

Nucleobase pairing following rules of complementarity is known to be useful in a variety of architectures. In solution, nucleobase pairing in the loop of a molecular beacon can open the beacon, separating a fluorescent species attached to one end of a hairpin structure from a quencher on the other. Pairing can assemble two DNA fragments transiently or covalently, as in a template-directed ligation. Pairing is useful for affixing an oligonucleotide that is free in solution to a support carrying the complementary oligonucleotide. The oligonucleotide can carry functional groups, including fluorescent groups attached to the nucleobases.

The Watson-Crick pairing rules can be understood chemically in terms of the arrangement of hydrogen bonding groups on the heterocyclic nucleobases of the oligonucleotide, groups that can either be hydrogen bond donors or acceptors. In the standard Watson-Crick geometry, a large purine nucleobase pairs with a small pyrimidine nucleobase. Thus, the AT nucleobase pair is the same size as a GC nucleobase pair. This means that the rungs of the DNA ladder, formed from either AT or GC nucleobase pairs, all have the same length.

Further recognition between nucleobases is determined by hydrogen bonds between the nucleobases. In standard nucleobases, hydrogen bond donors are heteroatoms (nitrogen or oxygen in the natural nucleobases) bearing a hydrogen, hydrogen bond acceptors are heteroatoms (nitrogen or oxygen in the natural nucleobases) with a lone pair of electrons. In the geometry of the Watson-Crick nucleobase pair, a six membered ring (in standard nucleobases, a pyrimidine) is juxtaposed to a ring system composed of a fused six membered ring and a five membered ring (in standard nucleobases, a purine), with a middle hydrogen bond linking two ring atoms, and hydrogen bonds on either side joining functional groups appended to each of the rings, with donor groups paired with acceptor groups.

In many applications, the nucleobases incorporated into one or more oligonucleotide analogs carry an appendage. In standard nucleobases, the appendage, or side chain, is attached to one or more pyrimidines at the 5-position, or at the 7-position of a 7-deazapurine, or to an exocyclic nitrogen, most often the exocyclic amino group of adenine or cytosine. Such nucleoside analogs have application because of their combination of Watson-Crick nucleobase pairing ability and the properties or reactivities associated with species appended via the side chain. For example, oligonucleotides containing a T to which is appended a side chain bearing a biotin residue can first bind to a complementary oligonucleotide, and the hybrid can then be isolated by virtue of the specific affinity of biotin to avidin [Langer, P. R., Waldrop, A. A., Ward, D. C. (1981) Proc. Nat. Acad. Sci. 78, 6633-6637]. This finds application in diagnostic work. Instead of biotin, the side chain can carry a fluorescent moiety, or a moiety that quenches the fluorescence of another moiety, a branching point, or a moiety that complexes to a metal, or a moiety that confers catalytic activity on the oligonucleotide, or a moiety that assists in the attachment of the oligonucleotide analog to a solid support, such as a bead, a one dimensional array, or a two dimensional array.

Often, derivatized standard nucleotides can be incorporated into oligonucleotides by enzymatic transcription of natural oligonucleotide templates in the presence of the triphosphate of the derivatized nucleoside, the substrate of the appropriate (DNA or RNA) polymerase, or a reverse transcriptase. In this process, a natural nucleoside is placed in the template, and standard Watson-Crick nucleobase pairing is exploited to direct the incoming modified nucleoside opposite to it in the growing oligonucleotide chain.

The standard available nucleobase pairs are limited in that they make available only two mutually exclusive hydrogen bonding patterns. This means that should one wish to introduce a modified nucleoside based on one of the natural nucleosides into an oligonucleotide, it would be incorporated wherever the complementary natural nucleoside is found in the template. For many applications, this is undesirable.

Further, in many applications, it would be desirable to have nucleobase pairs that behave as predictably as the AT (or U) and GC nucleobase pairs, but that do not cross-pair with natural oligonucleotides, which are built from A, T (or U), G, and C. This is especially true in diagnostics assays based. Biological samples generally contain many nucleic acid molecules in addition to the nucleic acid that one wishes to detect. The adventitious DNA/RNA, often present in abundance over the targeted analyte DNA (or RNA), is also composed of A, T (or U), G, and C. Thus, adventitious DNA/RNA can compete with the desired interactions between two or more oligonucleotide-like molecules.

Many of the limitations that arise from the existence of only four standard nucleobases, joined in only two types of nucleobase pairs via only two types of hydrogen bonding schemes, could be overcome were additional nucleobases available that could be incorporated into oligonucleotides. Here, the additional nucleobases would still pair in the Watson-Crick geometry, but would present patterns of hydrogen bond donating and accepting groups in a pattern different from those presented by the natural nucleobases. They therefore would form nucleobase pairs with additional complementary nucleobases in preference to (and, preferably, with strong preference to, meaning with at least a 10 to 100 fold affinity greater than to mismatched oligonucleotides or oligonucleotide analogs).

In the last decade, Benner disclosed compositions of matter that were intended to overcome the limitations of molecular recognition by changing the pattern of hydrogen bond donor and acceptor groups presented by a nucleobase to the nucleobase on a complementary oligonucleotide analog [U.S. Pat. Nos. 5,432,272, 5,965,364, 6,001,983, 6,037,120, 6,140,496, 6,627,456, 6,617,106]. These disclosures showed that the geometry of the Watson-Crick nucleobase pair can accommodate as many as 12 nucleobases forming 6 mutually exclusive pairs. Of these, 4 nucleobases forming two pairs are "standard", while 8 nucleobases forming four pairs are "non-standard". Adding the non-standard nucleobases to the standard nucleobases yielded an Artificially Expanded Genetic Information System (AEGIS). Specifically, structures shown in FIG. 1, from U.S. Pat. No. 6,140,496, implement the designated hydrogen bonding patterns. It was also noted that these nucleobases analogs may be functionalized to enable a single biopolymer capable of both genetics and catalysis. Expanded genetic alphabets have been explored in several laboratories, and the possibility of a fully artificial genetic system has been advanced [Switzer, C. Y., Moroney, S. E., Benner, S. A. (1989) Enzymatic incorporation of a new base pair into DNA and RNA. *J. Am. Chem. Soc.* 111, 8322-8323] [Piccirilli, J. A., Krauch, T., Moroney, S. E., Benner, S. A. (1990) Extending the genetic alphabet. Enzymatic incorporation of a new base pair into DNA and RNA. *Nature* 343, 33-37][Piccirilli, J. A., Krauch, T., MacPherson, L. J., Benner, S. A. (1991) A direct route to 3-(ribofuranosyl)-pyridine nucleosides. *Helv. Chim. Acta* 74, 397-406] [Voegel, J. J., Altorfer, M. M., Benner, S. A. (1993) The donor-acceptor-acceptor purine analog. Transformation of 5-aza-7-deaza-isoguanine to 2'-deoxy-5-aza-7-deaza-iso-guanosine using purine nucleoside phosphorylase. *Helv. Chim Acta* 76, 2061-2069] [Voegel, J. J., von Krosigk, U., Benner, S. A. (1993) Synthesis and tautomeric equilibrium of 6-amino-5-benzyl-3-methylpyrazin-2-one. An acceptor-donor-donor nucleoside base analog. *J. Org. Chem.* 58, 7542-7547][Heeb, N. V., Benner, S. A. (1994) Guanosine derivatives bearing an $N^2$-3-imidazolepropionic acid. *Tetrahedron Lett.* 35, 3045-3048] [Voegel, J. J., Benner, S. A. (1994) Non-standard hydrogen bonding in duplex oligonucleotides. The base pair between an acceptor-donor-donor pyrimidine analog and a donor-acceptor-acceptor purine analog. *J. Am. Chem. Soc.* 116, 6929-6930][von Krosigk, U., Benner, S. A. (1995) pH-independent triple helix formation by an oligonucleotide containing a pyrazine donor-donor-acceptor base. *J. Am. Chem. Soc.* 117, 5361-5362][Voegel, J. J., Benner, S. A. (1996) Synthesis, molecular recognition and enzymology of oligonucleotides containing the non-standard base pair between 5-aza-7-deaza-iso-guanine and 6-amino-3-methylpyrazin-2-one, a donor-acceptor-acceptor purine analog and an acceptor-donor-donor pyrimidine analog. *Helv. Chim. Acta* 79, 1881-1898] [Voegel, J. J., Benner, S. A. (1996) Synthesis and characterization of non-standard nucleosides and nucleotides bearing the acceptor-donor-donor pyrimidine analog 6-amino-3-methylpyrazin-2-one. *Helv. Chim. Acta* 79, 1863-1880][Kodra, J., Benner, S. A. (1997) Synthesis of an N-alkyl derivative of 2'-deoxyisoguanosine. *Syn. Lett.*, 939-940] [Jurczyk, S., Kodra, J. T., Rozzell, J. D., Jr., Benner, S. A., Battersby, T. R. (1998) Synthesis of oligonucleotides containing 2'-deoxyisoguanosine and 2'-deoxy-5-methyliso-cytidine using phosphor-amidite chemistry. *Helv. Chim. Acta* 81, 793-811][Lutz, S., Burgstaller, P., Benner, S. A. (1999) An in vitro screening technique for polymerases that can incorporate modified nucleotides. Pseudouridine as a substrate for thermostable polymerases. *Nucl. Acids Res.* 27, 2792-2798][Jurczyk, S. C., Battersby, T. R., Kodra, J. T., Park, J.-H., Benner, S. A. (1999) Synthesis of 2'-deoxyisoguanosine triphosphate and 2'-deoxy-5-methyl-isocytidine triphosphate. *Helv. Chim. Acta.* 82, 1005-1015] [Jurczyk, S. C., Horlacher, J., Devine, K. G., Benner, S. A., Battersby, T. R. (2000) Synthesis and characterization of oligonucleotides containing 2'-deoxyxanthosine using phosphoramidite chemistry. *Helv. Chim. Acta* 83, 1517-1524][Rao, P., Benner, S. A. (2001) A fluorescent charge-neutral analog of xanthosine: Synthesis of a 2'-deoxyribonucleoside bearing a 5-aza-7-deazaxanthine base. *J. Org. Chem.* 66, 5012-5015].

To systematize the nomenclature for the hydrogen bonding patterns, the hydrogen bonding pattern implemented on a small component of a nucleobase pair pare designated by the prefix "py". Following this prefix is the order, from the major groove to the minor groove, of hydrogen bond acceptor (A) and donor (D) groups. Thus, both thymine and uracil implement the standard hydrogen bonding pattern pyADA. The standard nucleobase cytosine implements the standard hydrogen bonding pattern pyDAA. Hydrogen bonding patterns implemented on the large component of the nucleobase pair are designated by the prefix "pu". Again following the prefix, the hydrogen bond donor and acceptor groups are designated, from the major to the minor grooves, using "A" and "D".

Thus, the standard nucleobases adenine and guanine implement the standard hydrogen bonding patterns puDA- and puADD respectively.

A central teaching of this disclosure is that hydrogen bonding pattern designated using this systematic nomenclature is distinct, in concept, from the organic molecule that is used to implement the hydrogen bonding pattern. Thus, guanosine is a nucleoside that implements the puADD hydrogen bonding pattern. So does, however, 7-deazaguanosine, 3-deazaguanosine, 3,7-dideazaguanosine, and any of any number of other purines and purine derivatives, including those that carry side chains to which are appended functional groups, such as fluorescent, fluorescent quencher, attachment, or metal complexing groups. Which organic molecule is chosen to implement a specific hydrogen bonding pattern determines, in large part, the utility of the non-standard hydrogen bonding pattern, in various applications to which it might be applied.

The structures disclosed by U.S. Pat. No. 6,140,496, as well as its predecessor patents, provide for an expanded molecular recognition system by providing more than four independently recognizable building blocks that can be incorporated into DNA and RNA.

Should the additional nucleobase pairs be placed into DNA and RNA, and if once so placed they have the desirable pairing properties, chemical stability, and other features known to those skilled in they art, they could be useful for a variety of purposes. For example, RNA molecules prepared by transcription, although it is known to be a catalyst under special circumstances [Cech, T. R., Bass, B. L (1986). *Ann. Rev. Biochem.* 55, 599][Szostak, J. W. (1986) *Nature* 332, 83. Been, M. D., Cech, T. R. (1988) *Science* 239, 1412], appear to have a much smaller catalytic potential than proteins because they lack building blocks bearing functional groups. Conversely, the limited functionality present on natural oligonucleotides constrains the chemist attempting to design catalytically active RNA molecules, in particular, RNA molecules that catalyze the template-directed polymerization of RNA.

Likewise, additional nucleobase pairs can be incorporated enzymatically at specific positions in an oligonucleotide molecule [Switzer, C. Y, Moroney, S. E., Benner, S. A. (1989) *J. Am. Chem. Soc.* 111, 8322]. If functionalized, such additional nucleobases should also allow the incorporation of functional groups into specific positions in a DNA or RNA sequence. A polymerase chain reaction has been demonstrated using a variant of an HIV reverse transcriptase to incorporate the pair between 2,4-diamino-5-(1'-beta-D-2'-deoxyribofuranosyl)-pyrimidine, implementing the pyDAD hydrogen bonding pattern, and 3,9-dihydro-9-(1'-beta-D-2'-deoxyribofuranosyl)-1H-purine-2,6-dione, implementing the puADA hydrogen bonding pattern [Sismour, A. M., Lutz, S., Park, J.-H., Lutz, M. J., Boyer, P. L., Hughes, S. H., Benner, S. A. (2004) PCR amplification of DNA containing non-standard base pairs by variants of reverse transcriptase from human immunodeficiency virus-1. *Nucl. Acids. Res.* 32, 728-735]. As standard nucleobases bearing functional groups at the 5-position of the uridine ring are accepted as substrates for most polymerases [Leary, J. L., Brigati, D. J., Ward, D. C. (1983) *Proc. Natl. Acad. Sci.* 80, 4045], non-standard nucleobases that are modified at the analogous positions are also accepted, provided that the polymerase accepts the parent non-standard nucleobase. New nucleobase pairs should also find use in studies of the structure of biologically important RNA and DNA molecules [Chen, T. R., Churchill, M. E. A. Tullius, T. D. Kallenbach, N. R., Seemann, N. C. (1988) *Biochem.* 27, 6032] and protein-nucleic acid interactions. They should also be useful in assembling nanostructures, including branched DNA useful for diagnostics, or for nanomachines. Further, non-standard nucleobases can be used to expand the genetic code, increasing the number of amino acids that can be incorporated translationally into proteins [Bain, J. D., Chamberlin, A. R., Switzer, C. Y., Benner, S. A. (1992) Ribosome-mediated incorporation of non-standard amino acids into a peptide through expansion of the genetic code. *Nature* 356, 537-539].

Some commercial applications have already been realized with the expanded genetic information systems disclosed by Benner in his patents. For example, the nucleobase pair between 2-amino-5-methyl 1-(1'-beta-D-2'-deoxyribofuranosyl)-4(1H)-pyrimidinone, also known as 2'-deoxyisocytidine, disoC, or sometimes (less correctly) isoC and implementing the pyAAD hydrogen bonding pattern, and 6-amino-1,9-dihydro-9-(1'-beta-D-2'-deoxyribofuranosyl)-3H-purin-2-one, also known as 2'-deoxyisoguanosine, disoG, or sometimes (less correctly) isoG, and implementing the puDDA hydrogen bonding pattern, is incorporated into the branched DNA diagnostics tools marketed today by Bayer. Here, it provides molecular recognition on demand in aqueous solution, similar to nucleic acids but with a coding system that is orthogonal to the system in DNA and RNA, Thus, it prevents the assembly of the branched dendrimer in the assay from being inhibited by adventitious nucleic acid, and prevents adventitious nucleic acid from capturing signaling elements form the nanostructure in the absence of the target analyte nucleic acid, creating noise. Further, adding extra letters to the genetic alphabet speeds hybridization, presumably because it decreases the number of close mismatches where DNA dwells before finding its correct, fully matched partner. The branched DNA assay now has FDA-approval, and is widely used to provide personalized patient care in the clinic.

The Benner patents claimed a wide range of structures generally, but only a few specifically. The compounds specifically claimed, where those claims were supported by specific examples in the disclosure, were disclosed as the preferred implementations of the individual hydrogen bonding patterns, and are reproduced in FIG. 1 (taken from FIG. 2 of U.S. Pat. No. 6,140,496). Making reference to U.S. Pat. No. 6,140,496, the following implementations (where a systematic name is given for the 2'-deoxyribonucleoside, the corresponding ribonucleosides, 2'-O-methyl ribonucleosides, and various derivatives of these were also disclosed) were preferred as implementations for each of the hydrogen bonding patterns:

For the pyDAD hydrogen bonding pattern. The preferred embodiment disclosed in U.S. Pat. No. 6,140,496 implemented the pyDAD hydrogen bonding pattern on the 2,4-diaminopyrimidine heterocycle. The specific deoxyribonucleoside was 2,4-diamino-5-(1'-beta-D-2'-deoxyribofuranosyl)-pyrimidine, also named (1R)-1,4-anhydro-2-deoxy-1-C-(2,4-diamino-5-pyrimidinyl)-D-erythropentitol.

For the puADA hydrogen bonding pattern. The preferred embodiment disclosed in U.S. Pat. No. 6,140,496 implemented the pyDAD hydrogen bonding pattern on the xanthine heterocycle. The specific deoxyribonucleoside was 3,9-dihydro-9-(1'-beta-D-2'-deoxyribofuranosyl)-1H-purine-2,6-dione, also known as 9-(2'-deoxy-beta-D-ribosyl)-xanthine.

For the pyAAD hydrogen bonding pattern. The preferred embodiment disclosed in U.S. Pat. No. 6,140,496 implemented the pyDAD hydrogen bonding pattern on the 5-methyl-isocytosine heterocycle. The specific deoxyribonucleoside was 2-amino-5-methyl-1-(1'-beta-D-2'-deoxyribofuranosyl)-4(1H)-pyrimidinone, For the puDDA hydrogen bonding pattern. The preferred embodiment disclosed in U.S. Pat. No. 6,140,496 implemented the pyDAD hydrogen bonding pattern on the isoguanine heterocycle. The specific deoxyribonucleoside was 6-amino-1,9-dihydro-9-(1'-beta-D-2'-deoxyribofuranosyl)-3H-purin-2-one.

For the pyDDA hydrogen bonding pattern. The preferred embodiment disclosed in U.S. Pat. No. 6,140,496 implemented the pyDAD hydrogen bonding pattern on the 6-amino-5-methyl-2(1H)-pyrazinone heterocycle. The specific deoxyribonucleoside was 6-amino-5-methyl-3-(1'-beta-D-2'-deoxyribofuranosyl)-2(1H)-pyrazinone.

For the puAAD hydrogen bonding pattern. The preferred embodiment in U.S. Pat. No. 6,140,496 implemented the pyDAD hydrogen bonding pattern on the 5-aza-3,7-dideazaguanosine heterocycle. The specific deoxyribonucleoside was 2-amino-1,9-dihydro-5-aza-3,7-dideaza-9-(1'-beta-D-2'-deoxyribofuranosyl)-1H-purin-6-one, also known as 7-amino-9-(1'-beta-D-2'-deoxyribofuranosyl)-imidazo[1,2-c]pyrimidin-5(1H)-one.

For the pyADD hydrogen bonding pattern. The preferred embodiment disclosed in U.S. Pat. No. 6,140,496 implemented the pyDAD hydrogen bonding pattern on the 6-amino-3-methyl-2(1H)-pyrazinone heterocycle. The specific deoxyribonucleoside was 6-amino-3-methyl-5-(1'-beta-D-2'-deoxyribofuranosyl)-2(1H)-pyrazinone, For the puDAA hydrogen bonding pattern. The preferred embodiment disclosed in U.S. Pat. No. 6,140,496 supported the pyDAD hydrogen bonding pattern on the 4-amino-1,3,5-triazin-2(8H)-one heterocycle. The specific deoxyribonucleoside was 4-amino-8-(2-deoxy-beta-D-erythro-pentofuranosyl)-imidazo[1,2-a]-1,3,5-triazin-2(8H)-one, also known as, 4-amino-8-(1'-beta-D-2'-deoxyribofuranosyl)-imidazo[1,2-a]-1,3,5-triazin-2(8H)-one.

Despite the value of the compositions disclosed by U.S. Pat. No. 6,140,496, it is clear that the specific compositions used to implement the various non-standard hydrogen bonding patterns were not optimal, at least from the perspective of potential utility. For example, the three hydrogen bonds that join the nucleobase pairs, both standard and non-standard, within a Watson Crick geometry are often to weak to bind two oligonucleotides containing them together under conditions that have utility. Adding an electron withdrawing group to an exocyclic amine permits the amino group (now part of an amide) to be a better hydrogen bond donor, therefore making a stronger nucleobase pair. Further, hydrogen bonding units can be extended into the major groove, forming a multiple ring system that allows nucleobase pairs to be joined by four hydrogen bonds. The notion of architectures where nucleobase pairs are joined by four hydrogen bonds was considered by Minakawa et al. [Noriaki Minakawa, Naoshi Kojima, Sadao Hikishima, Takashi Sasaki, Arihiro Kiyosue, Naoko Atsumi, Yoshihito Ueno, Akira Matsuda (2003) New base pairing motifs. The synthesis and thermal stability of oligodeoxynucleotides containing imidazopyridopyrimidine nucleosides with the ability to form four hydrogen bonds. J. Am. Chem. Soc. 125, 9970-99821 [Minakawa, Noriaki; Hikishima, Sadao; Matsuda, Akira (2004) Preparation of bicyclic naphthyridine nucleosides. PCT Int. Appl. (2004), 36 pp. CODEN: PIXXD2 WO 2004048376 A1 20040610 CAN 141:54575 AN 2004:467890][Czernek, J. (2004) Imidazopyridopyrimidine base pairing motifs consisting of four hydrogen bonds: a quantum chemical study. Chem. Phys. Letters 392, 508-513.] The compositions in their invention differ from those described here in that the ring system is extended to the minor groove. The instant invention teaches that the major groove is a preferred site to fuse rings to support additional hydrogen bonding groups.

Further, Cook et al. have described a complicated set of tricyclic structures in an international filing [Cook, P. D., Ewing, G., Jin, Y., Lambert, J., Prhavc, M., Rajappan, V., Rajwanshi, V. K., Sakthivel, K. (2005) WO 2005/0215681. While it is not entirely clear what compositions and processes this publication discloses, it appears that the publication is targeted towards compositions proposed to have utility as antiviral agents, does not disclose nucleobase pairing, non-standard structures, or any other of the inventive features of the instant application.

DESCRIPTION OF INVENTION

This invention describes nucleobase analogs that, when incorporated as nucleotides into an oligonucleotide strand (DNA or RNA, but also backbone modified DNA and RNA structures, and analog backbones, such as PNA), are able to form four hydrogen bonds with a complementary nucleobase analog incorporated into a complementary strand, instead of the standard three, where the extra hydrogen bond is obtained by an extension of the nucleobase analog into the major groove on both components.

Figure 1:
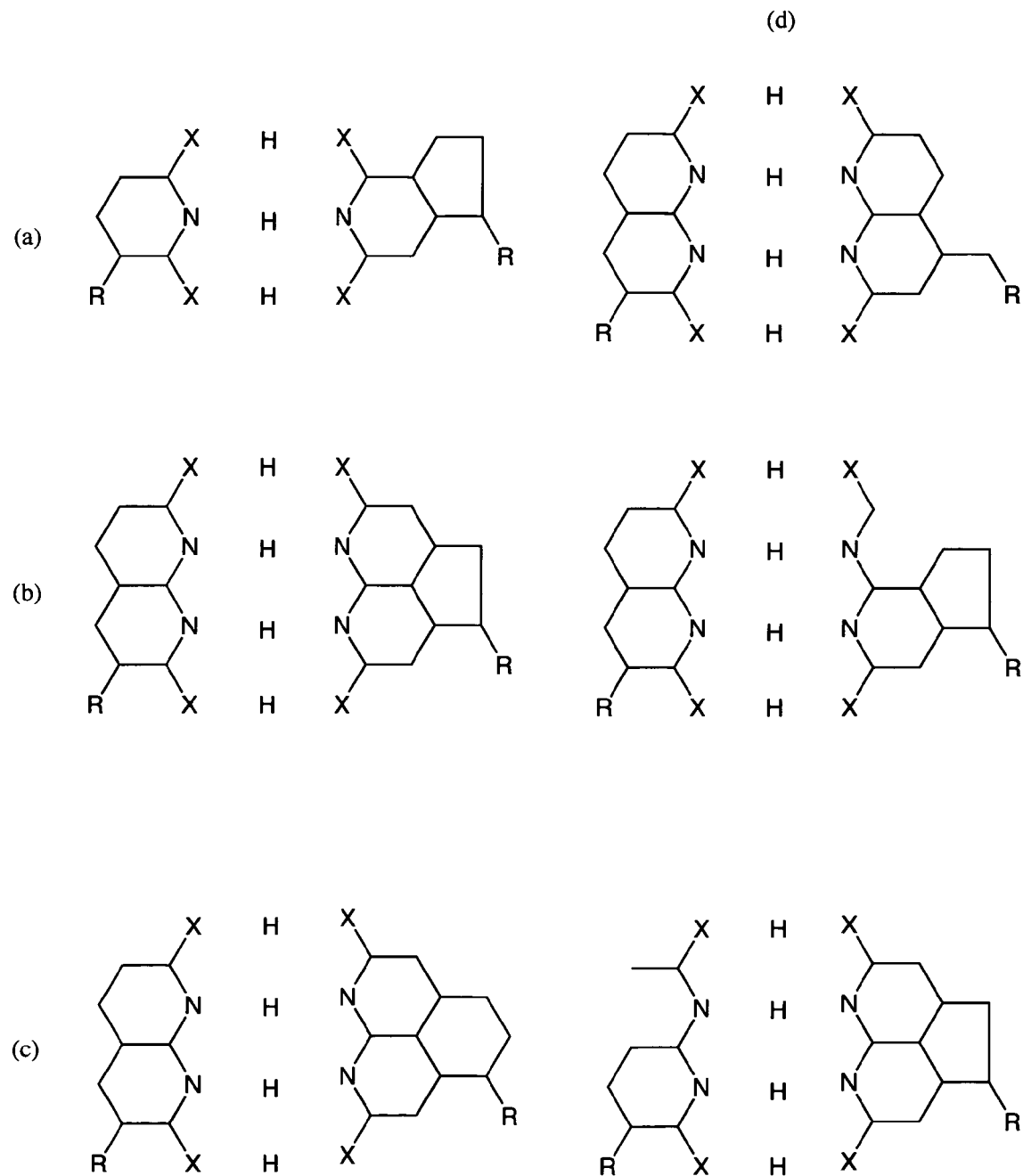
FIG. 1. (a) A schematic description of the standard Watson-Crick nucleobase pair, joined by three hydrogen bonds. The X's represent heteroatoms, generally N or O, that can act as hydrogen bond donors or acceptors. If the X is a hydrogen bond donor, then the hydrogen, represented by an H in the middle of the pair, is covalently bonded to it. If X is not a hydrogen bond donor, then the hydrogen is covalently bonded to the paired X on the partner nucleobase. Other heteroatoms and double bonds in the ring are distributed to alter the pattern of hydrogen bond donor and accept or groups, as in the AEGIS design. Double bonds, nitrogen atoms, and substituents are also incorporated in or appended on the system at places that do not form hydrogen bonds to the complementary base to achieve stability, aromaticity, or functionality as required for application, as is well known in the art. (b) The same, but in a structure that forms four hydrogen bonds. Here the pyrimidine and purine analogs each have an additional six-membered ring fused to the core structure. (c) The same, but where the purine analog has three six-membered rings. (d) The same, but teaching that a variety of "seco" structures, where one atom is missing from one of the rings, can also support a nucleobase pairing strategy where the two components of the pairs are joined by four hydrogen bonds. R is ribose or 2'-deoxyribose, their triphosphates, their protected 5'-phosphoramidites, their protected 3'-phosphoramidites, and other species known in the art.
Figure 2A:
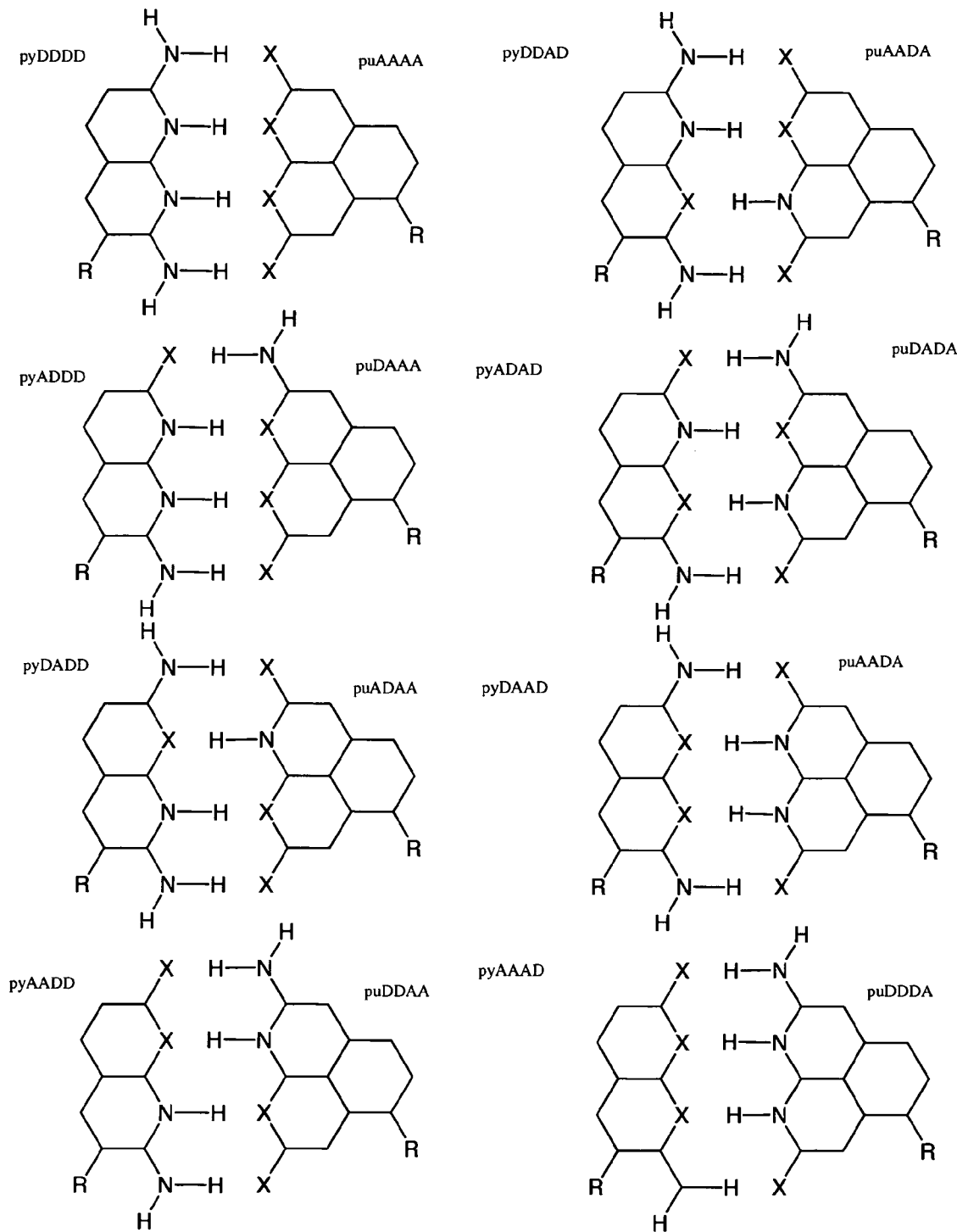
FIG. 2. The 16 different nucleobase pairs with the appropriate nomenclature. The generic structures are named using the nomenclature described in the text, where the purine analog is chosen from the general six-six-six ring system shown in FIG. 1 (c). The analogous hydrogen bonding patterns can be achieved on the other scaffolds, including the seco scaffolds, shown in FIG. 1. Atoms not specified in the structure can vary depending on the specific heterocyclic system used to implement the indicated hydrogen bonding scheme. R is ribose or 2'-deoxyribose, their triphosphates, their protected 5'-phosphoramidites, their protected 3'-phosphoramidites, and other species known in the art.
Figure 2B:
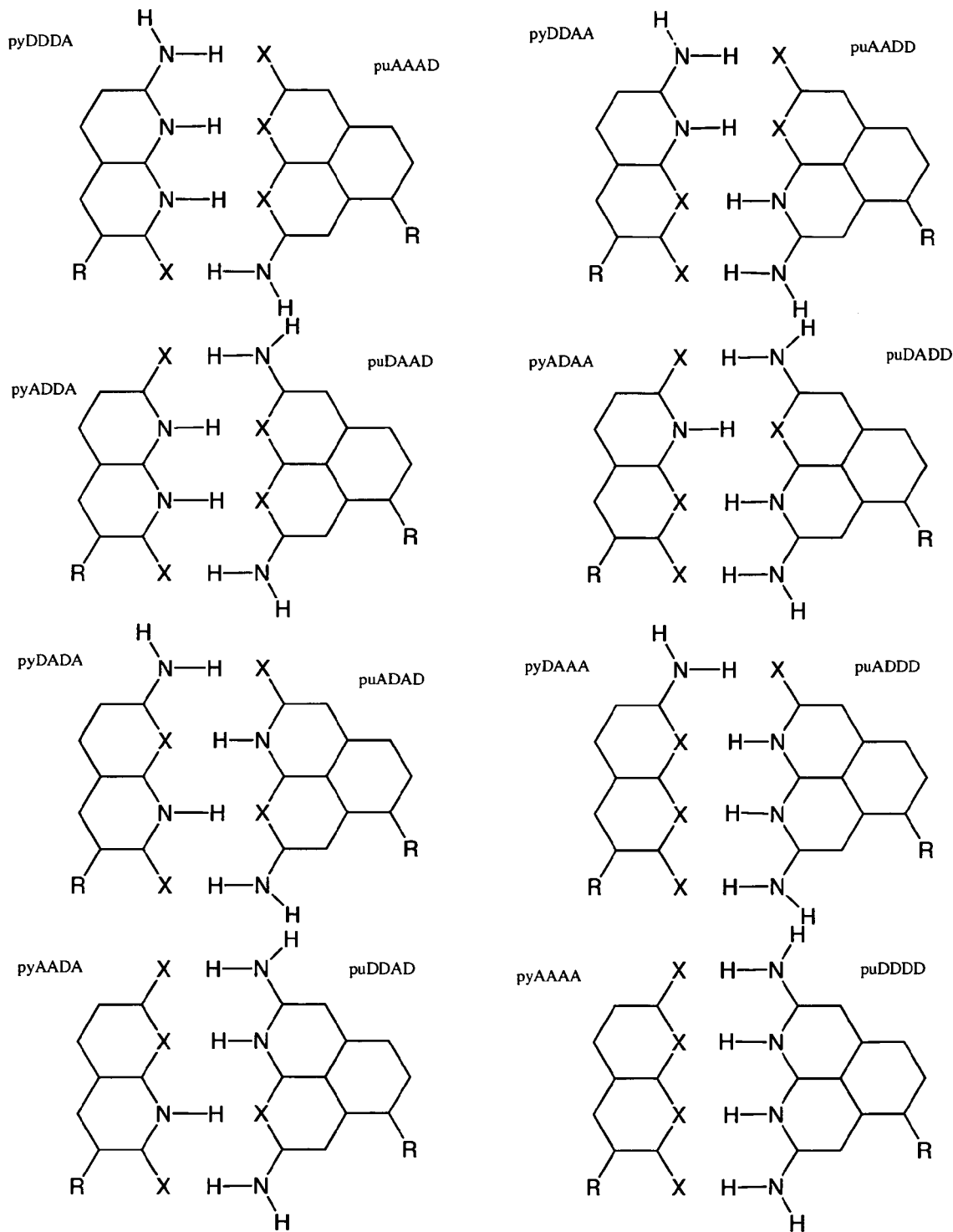
Figure 3:
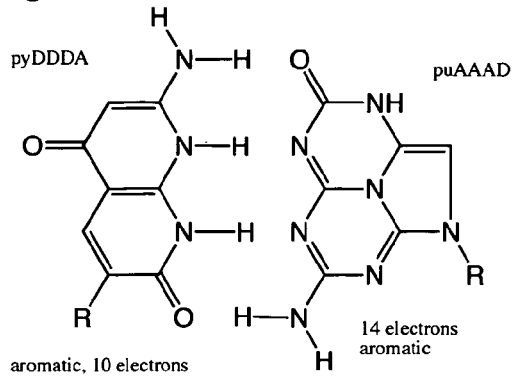
FIG. 3. A set of heterocycle pairs that implement various hydrogen bonding patterns on pyrimidine and purine analogs that form nucleobase pairs joined by four hydrogen bonds. Comments indicate sources of the compounds, in cases where the literature contains the heterocycle, or precursors for the compounds, in cases where the specific heterocycle is not known. Some of the compounds implementing the particular hydrogen bonding pattern are noted to have alternative tautomeric forms. These can serve as semi-universal nucleobases. R is ribose or 2'-deoxyribose, their triphosphates, their protected 5'-phosphoramidites, their protected 3'-phosphoramidites, and other species known in the art. In each of these examples, the pyrimidine analog presents an unshared pair of electrons in the minor groove.
Figure 3:
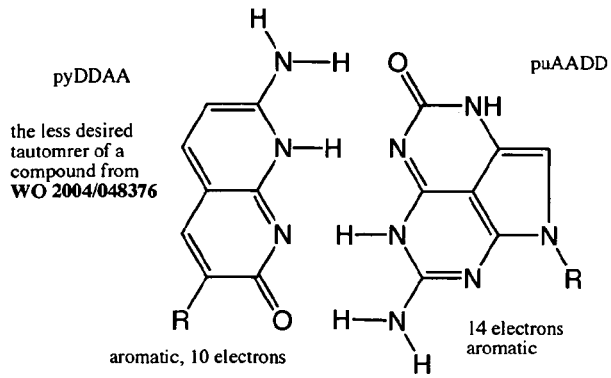
Figure 3:
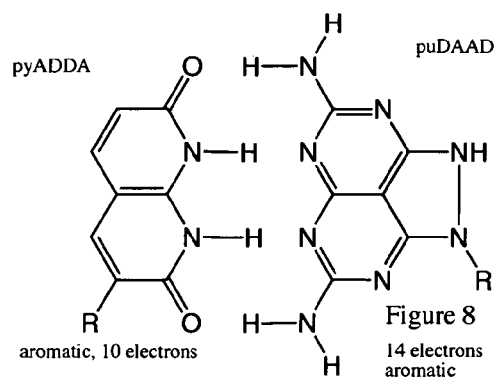
Figure 3:
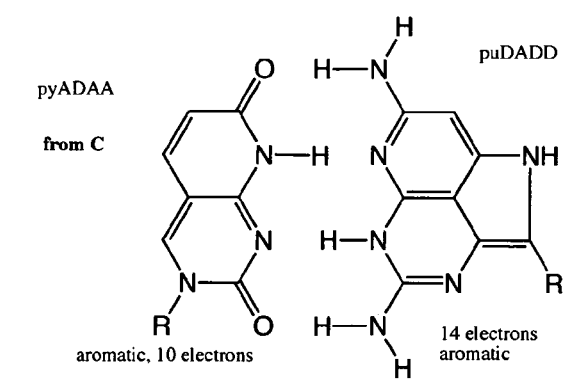
Figure 3:
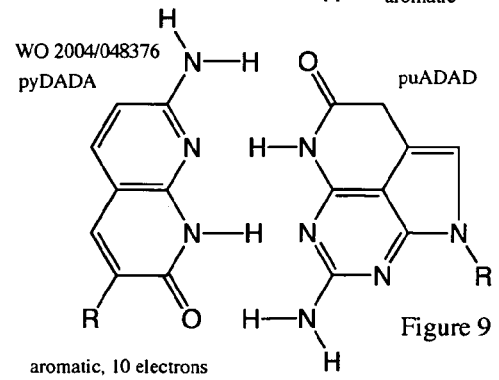
Figure 3:
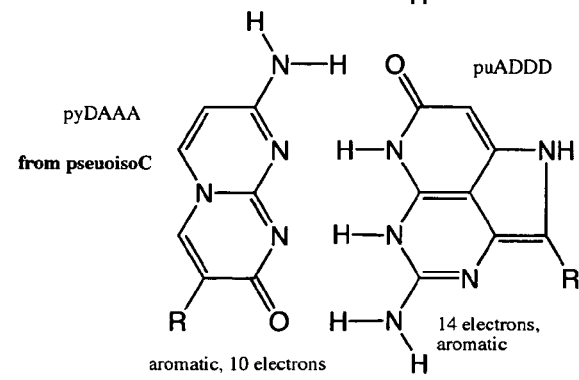
Figure 3:
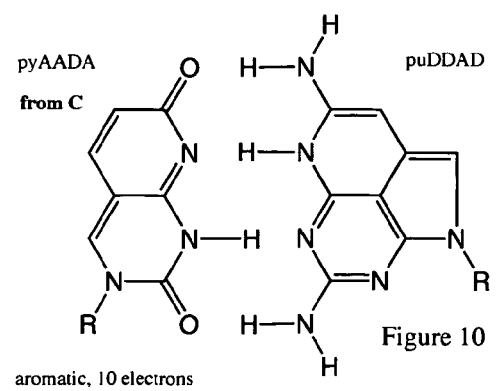
Figure 3:
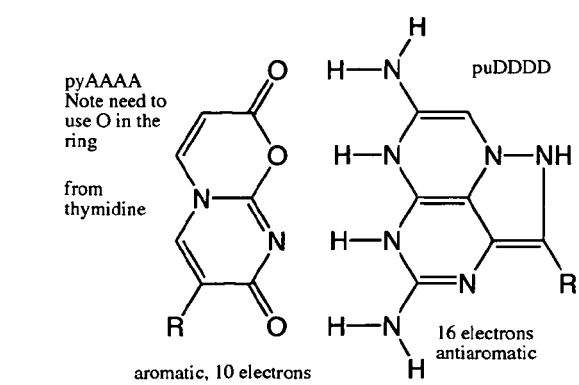
Figure 4:
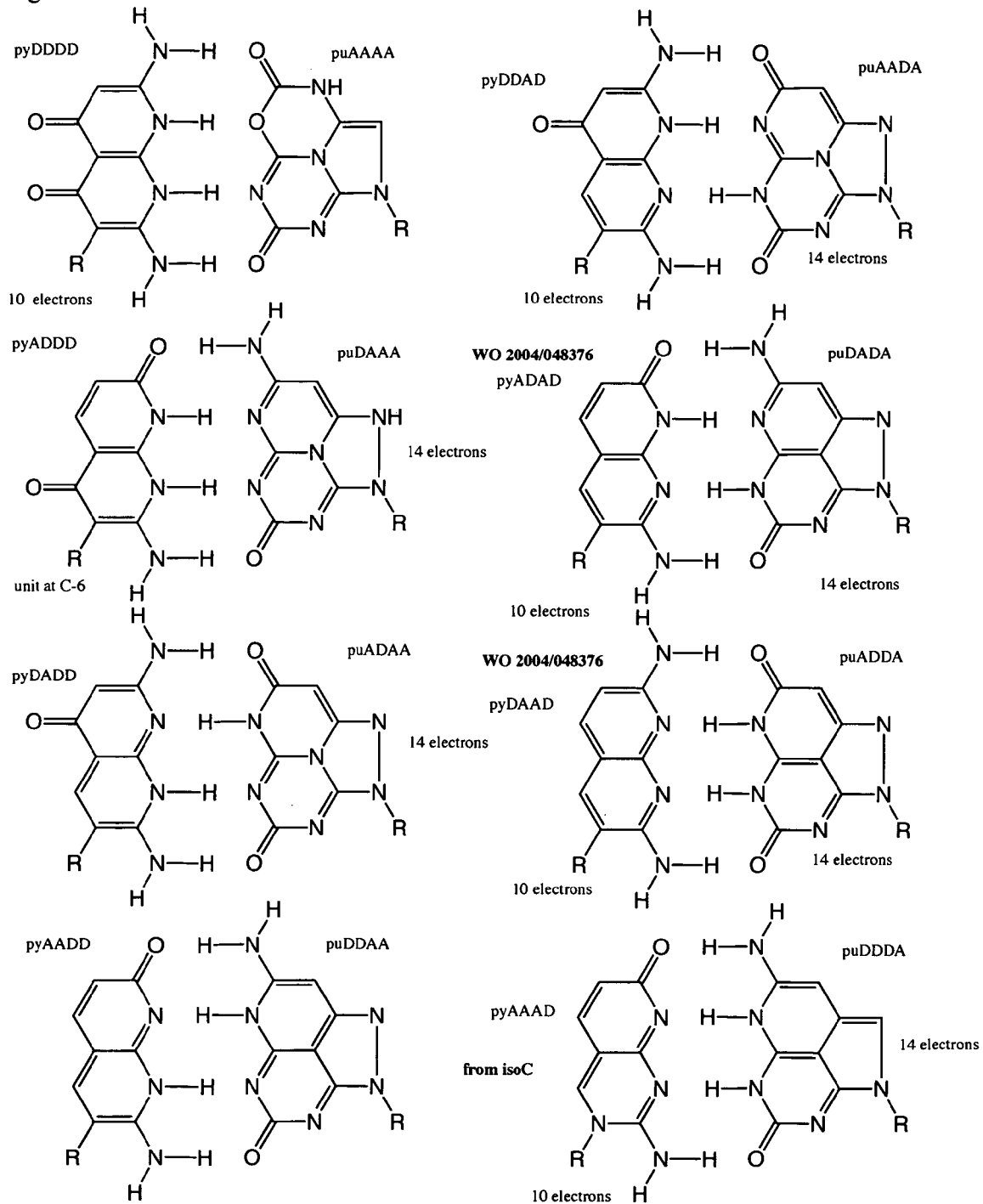
FIG. 4. Another set of heterocycle pairs that implement various hydrogen bonding patterns on pyrimidine and purine analogs that form nucleobase pairs joined by four hydrogen bonds. Comments indicate sources of the compounds, in cases where the literature contains the heterocycle, or precursors for the compounds, in cases where the specific heterocycle is not known. Some of the compounds implementing the particular hydrogen bonding pattern are noted to have alternative tautomeric forms. These can serve as semi-universal nucleobases. R=ribose or 2'-deoxyribose, their triphosphates, their protected 5'-phosphoramidites, their protected 3'-phosphoramidites, and other species known in the art.

The nomenclature used in this specification is analogous to nomenclature one used for AEGIS outlined in the introduction, to describe the possible nucleobase pairs that involve four hydrogen bonding through extension into the major groove. As before, the pyrimidine analogs carry the prefix "py", and the purine analogs carry the prefix "pu". As before, the hydrogen bonding groups are specified as donor "D" or acceptor "A", proceeding from the major groove to the minor groove. In each case, the analog has an extra fused ring, when compared to the standard species. While the additional fused ring need not be a six-membered ring, we illustrate the invention here by examples where a six-membered ring is the additional fused ring. The generic structure is shown in FIG. 1. More specific details, and all of the hydrogen bonding patterns, are shown in FIG. 2. Various implementations of the hydrogen bonding patterns are shown in FIG. 3 and FIG. 4.

A large number of hydrogen bonding patterns (2×2×2×2=16, supported by a total of 32 compounds, half of these being purine analogs, the other half being pyrimidine analogs) are possible when four hydrogen bonding elements are used. Further, each of the hydrogen bonding elements can be implemented on a number of different heterocycles. These come from different placement of heteroatoms within the ring system, different arrangements of double bonds, and different functionality placed at positions in the ring system that do not interact with the complementary nucleobase in the extended Watson-Crick nucleobase pair.

To determine which of these is preferred, this disclosure teaches several easily implemented rules.

1. For different implementations of a particular hydrogen bonding pattern, a placement of heteroatoms in the system that renders the system Hueckel aromatic is preferred over a placement that does not.

2. For different implementations of a particular hydrogen bonding pattern, a placement of a heteroatom in a position analogous to the N-3 position of a purine is preferred over a placement that does not.

3. For different implementations of a particular hydrogen bonding pattern, a placement of a heteroatom in a position that creates an N-glycoside is preferred over a placement that does not.

4. For different implementations of a particular hydrogen bonding pattern, a placement of a heteroatom in a position that creates no tautomeric ambiguity is preferred over a placement that does.

5. For different implementations of a particular hydrogen bonding pattern, an implementation that does not place an exocyclic unit larger than hydrogen in a position that is analogous to C-5 of pyrimidines or C-8 of purines is preferred over an implementation that does.

6. The appended ring may contain units that interrupt the conjugation (such as $CH_2$ units), and is preferred to contain these is the system would otherwise be antiaromatic.

Figure 6:
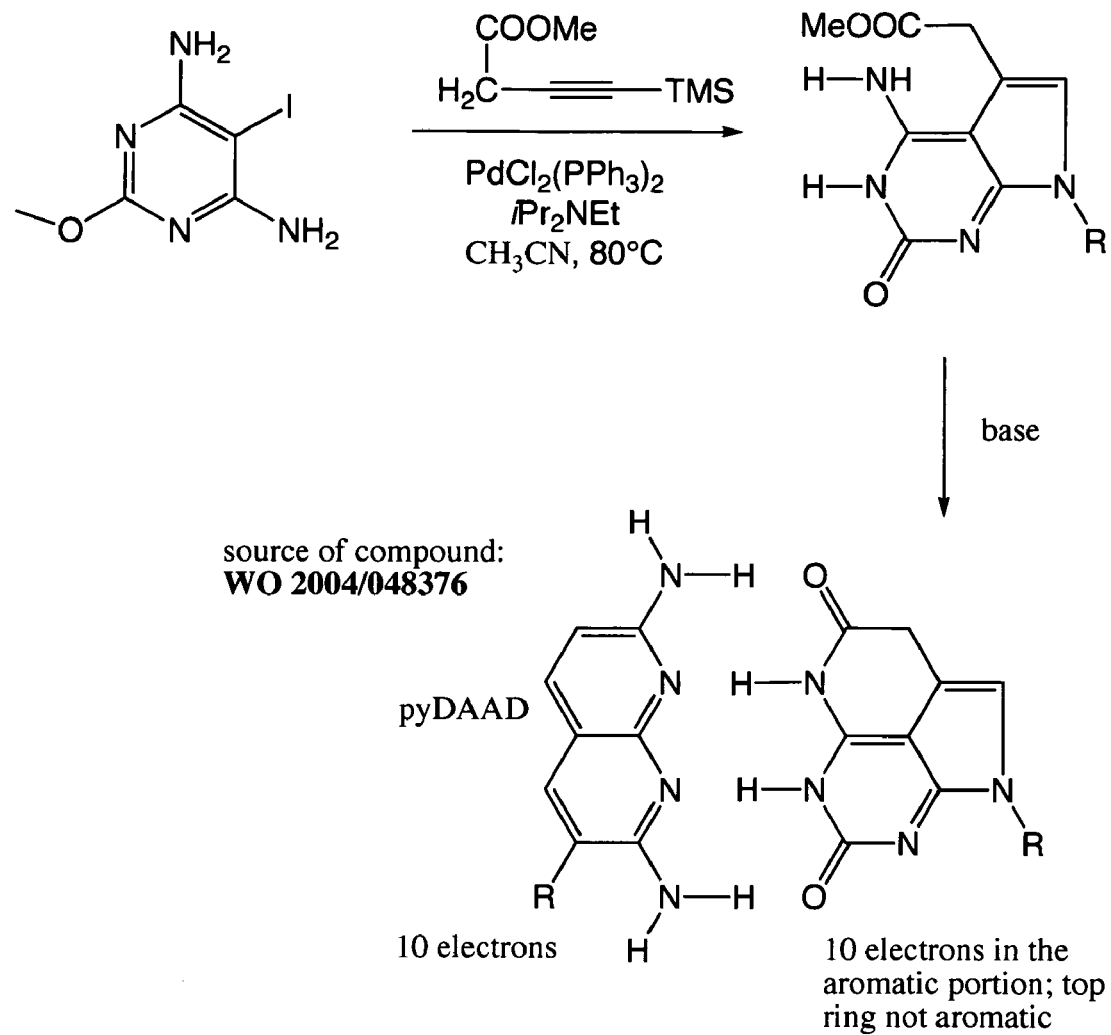
FIG. 6. Two compounds, and routes for their synthesis, that implement the nucleobase pair represented in the nomenclature as pyDAAD-puADDA. The route for the synthesis of the puADDA component is adapted from the Martinot dissertation. The pyDAAD species is described in WO 2004/048376.
Figure 7:
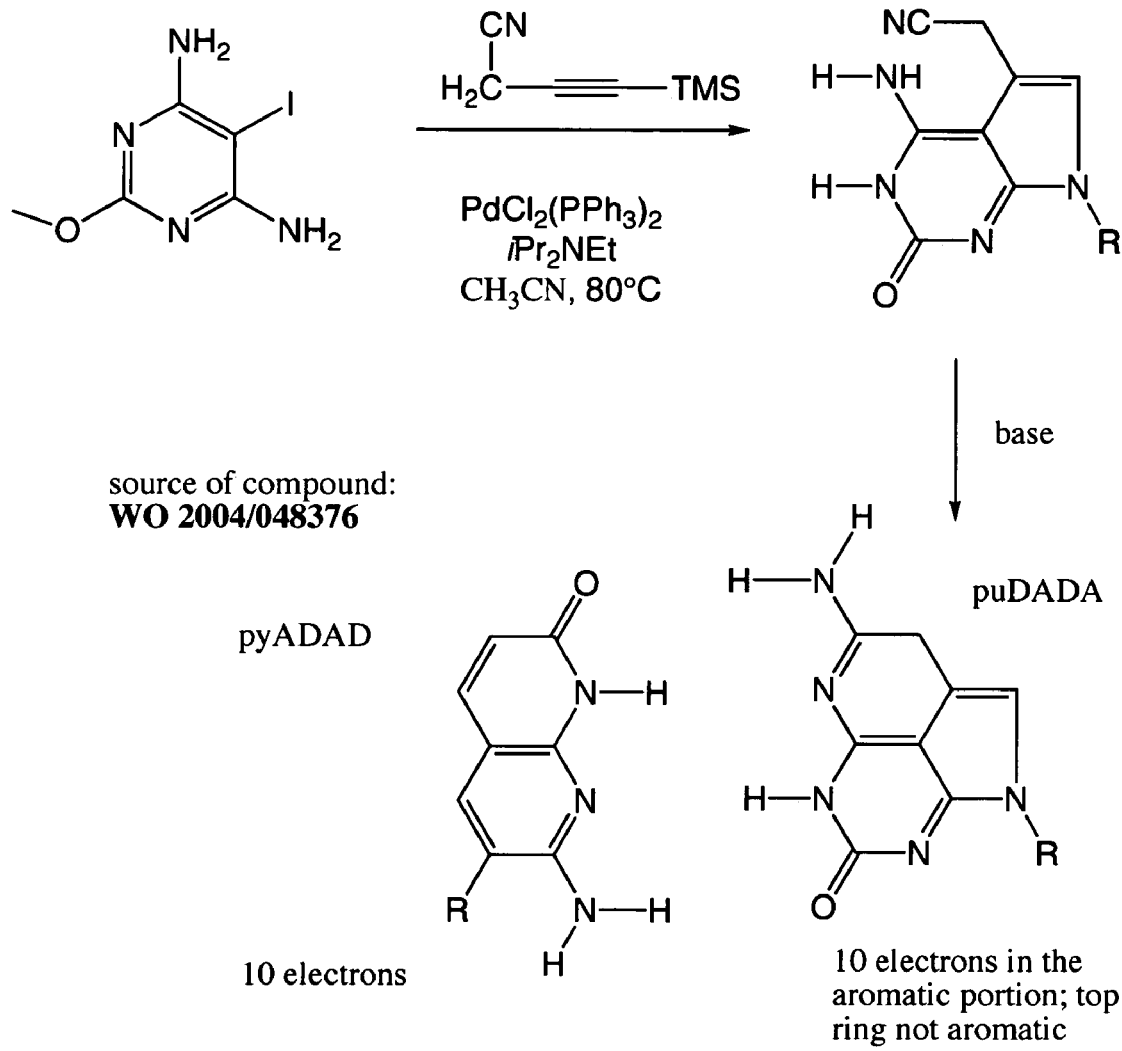
FIG. 7. Two compounds, and routes for their synthesis, that implement the nucleobase pair represented in the nomenclature as pyADAD-puDADA. The route for the synthesis of the puADDA component is adapted from the Martinot dissertation. The pyADAD species is described in WO 2004/048376.
Figure 8:
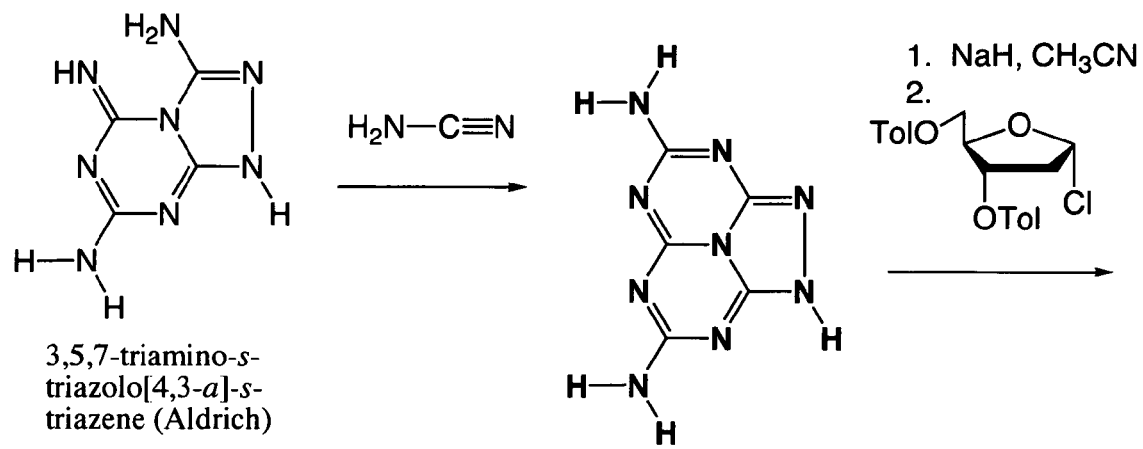
FIG. 8. Two compounds, and routes for their synthesis, that implement the nucleobase pair represented in the nomenclature as pyADDA-puDAAD. The synthesis of the puDAAD component begins with a commercially available triazene. The pyADDA species is described in WO 2004/048376.
Figure 8:
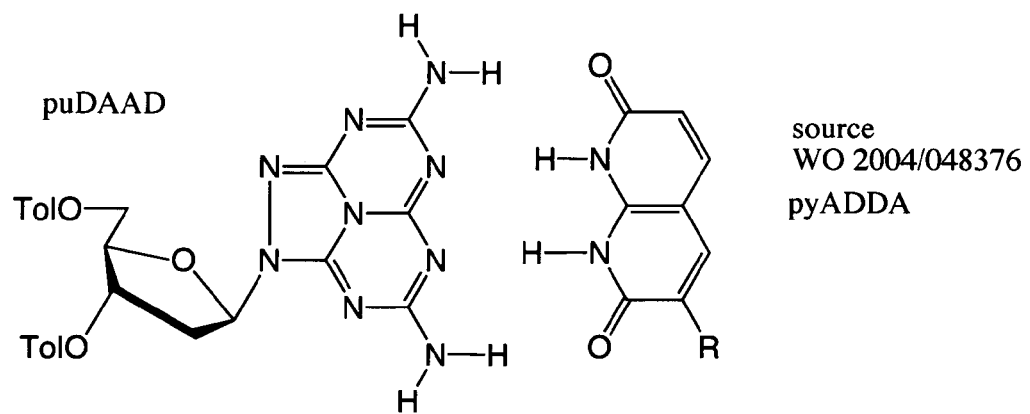
Figure 9:
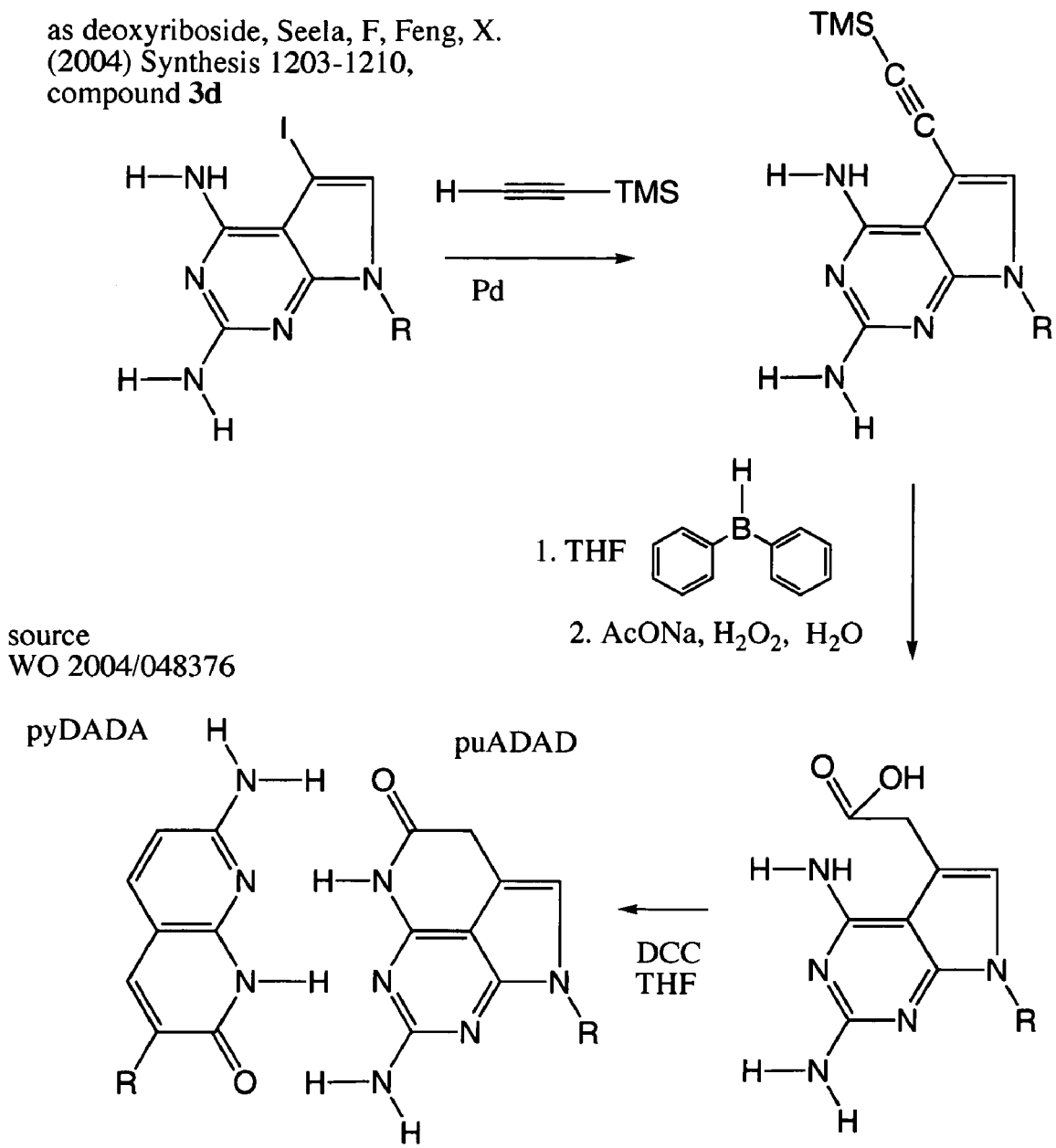
FIG. 9. Two compounds, and routes for their synthesis, that implement the nucleobase pair represented in the nomenclature as pyDADA-puADAD. The synthesis of the puADAD component begins with a compound reported as deoxyriboside 3d in the paper: [Seela, F, Feng, X. (2004) Regioselective synthesis of 7-halogenated 7-deazapurine nucleosides related to 2-amino-7-deaza-3'-deoxyadenosine and 7-deaza-2'-deoxyisoguanosine. Synthesis 1203-1210. The pyDADA species is described in WO 2004/048376.
Figure 10:
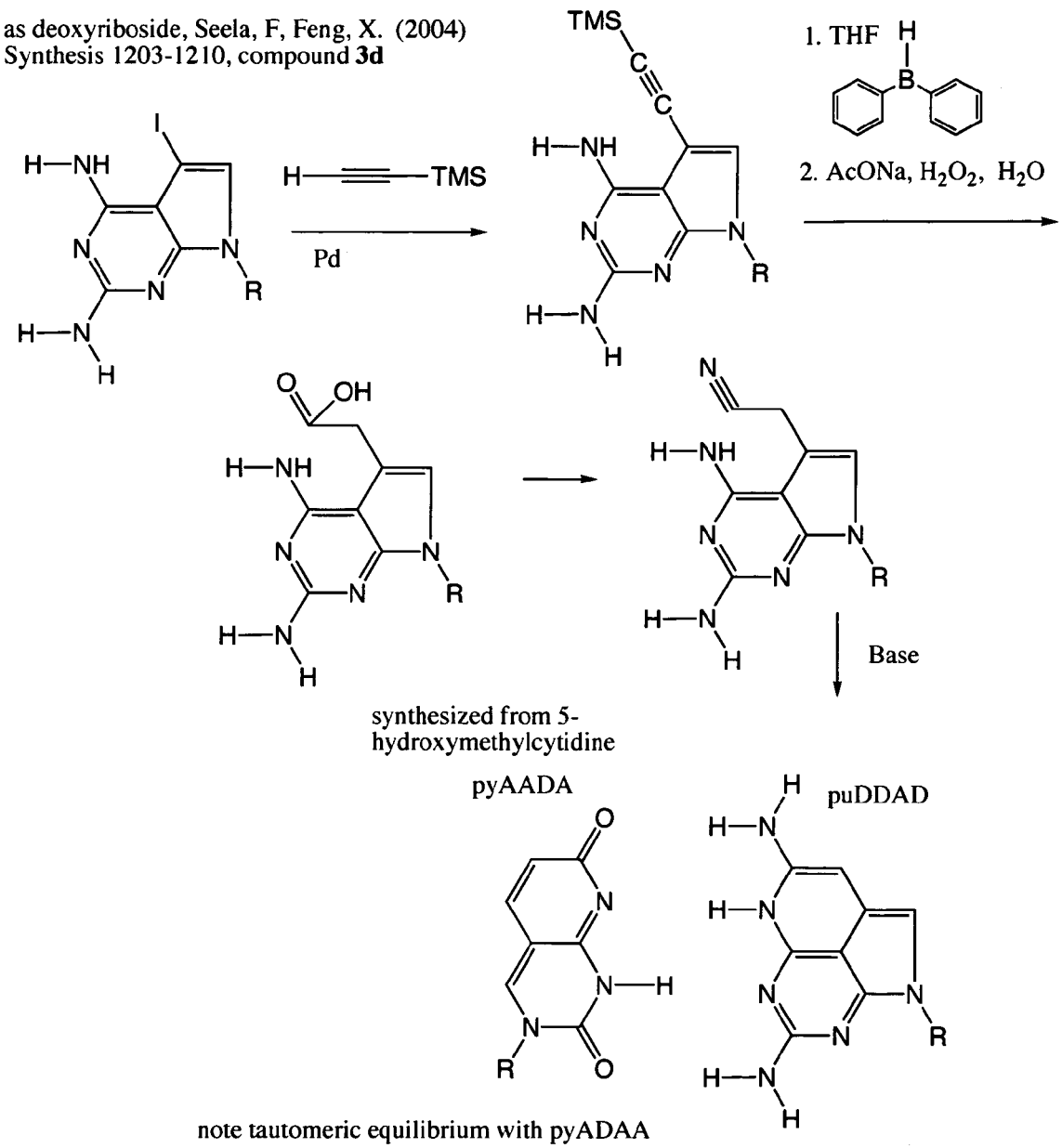
FIG. 10. Two compounds, and routes for their synthesis, that implement the nucleobase pair represented in the nomenclature as pyAADA-puDDAD. The synthesis of the puADAD component begins with a compound reported as deoxyriboside 3d in the paper: [Seela, F, Feng, X. (2004) Regioselective synthesis of 7-halogenated 7-deazapurine nucleosides related to 2-amino-7-deaza-3'-deoxyadenosine and 7-deaza-2'-deoxyisoguanosine. *Synthesis* 1203-1210]. The pyAADA species is synthesized by converting 5',3'-diprotected 2'-deoxy-5-hydroxymethylcytidine to the aldehyde, and aldol condensation with an acetate derivative.

A sample of various implements is shown in the drawings. For example, it is difficult to obtain a pyrimidine analog that implements the pyAAAA hydrogen bonding pattern using only N and O as heteroatoms, standard valence rules, and no charges (using Cl atoms as the hydrogen bond acceptors, of course, one might implement this hydrogen bonding pattern on a dichlorodiazanapthalene ring system). Routes to prepare various implementations are shown in the Drawings, starting with FIG. 6.

EXAMPLES

Example 1

Figure 5:
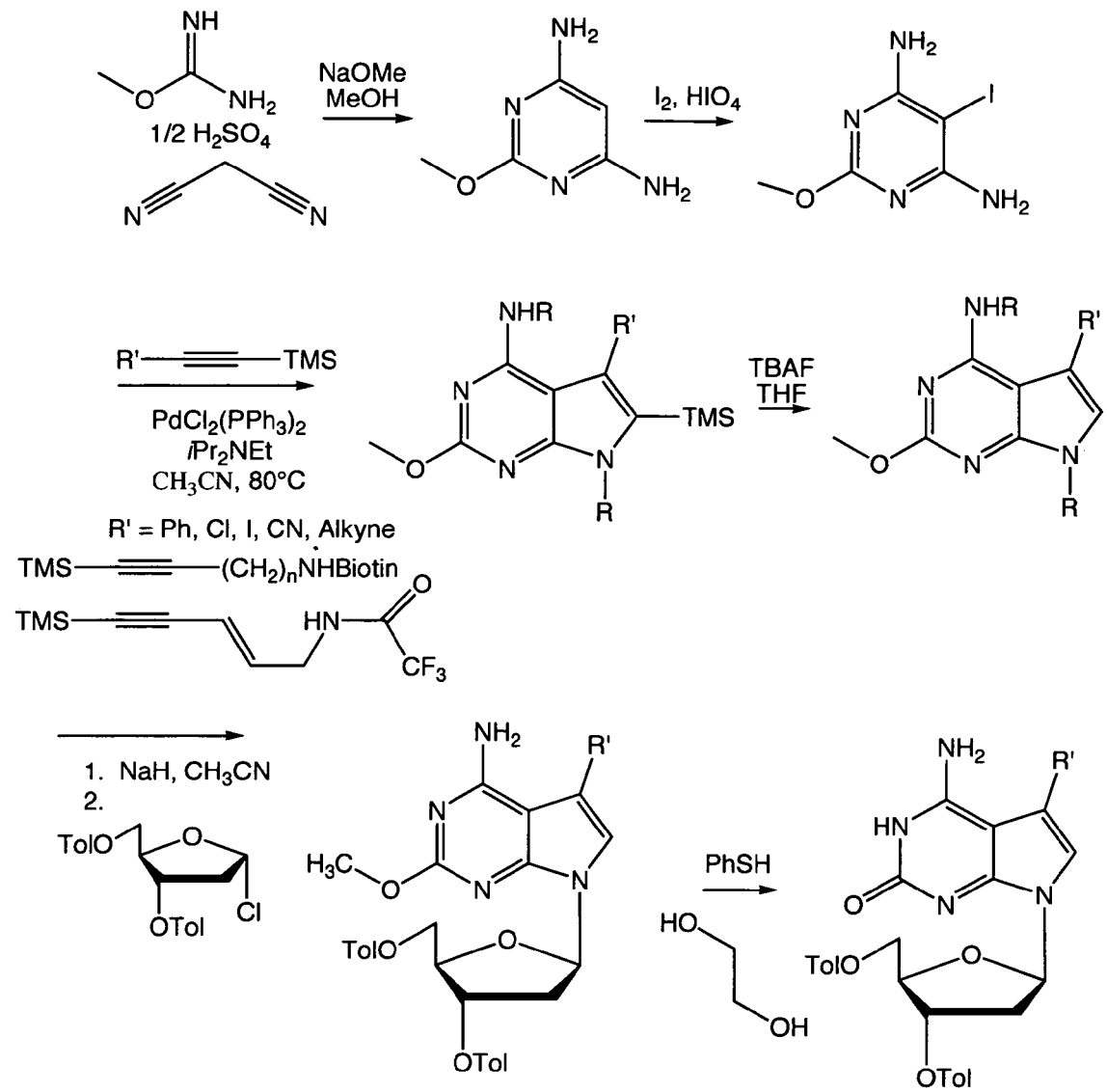
FIG. 5. The general route to substituted isoguanosine-2'-deoxyribosides developed by Martinot [Martinot, T. A. (2004) From sugars to nucleic acids: Synthesis of an n-linked inositol dimer and advances toward a fully functional expanded genetic information system. Dissertation, University of Florida].

The substituted 7-deazaisoguanosine derivatives in the 2'-deoxyriboside forms are known from the dissertation of Theodore Martinot (University of Florida, 2004), and the synthesis of this compound is outlined in FIG. 5. Some details of the procedure are given below:

2,2,2-Trifluoro-N-(5-trimethylsilanyl-pent-2-en-4-ynyl)-acetamide

N-(3-Chloro-allyl)-2,2,2-trifluoro-acetamide (863 mg, 4.62 mmol) is dissolved in piperidine (3 mL), and dichlorobis (triphenylphosphine)palladium (131 mg, 0.19 mmol), and copper(I) iodide (60 mg, 0.32 mmol) are added under nitrogen. After 2 min., the solution turns light green, and TMS-acetylene (1 mL) is then added. The solution is allowed to stir overnight at RT under nitrogen, after which mixture is dark red. The reaction mixture is concentrated under reduced pressure, loaded onto a silica gel column, and purified using flash column chromatography with methylene chloride as the solvent to give the product as a colorless oil. $R_f$ 0.5 (80:20-hexanes:ethyl acetate)

N-[3-(4-Amino-2-methoxy-6-trimethylsilanyl-7H-pyrrolo[2,3-d]pyrimidin-5-yl)-allyl]-2,2,2-trifluoro-acetamide 5-Iodo-2-methoxy-pyrimidine-4,6-diamine (3.267 g, 12.28 mmol) is dissolved in acetonitrile (50 mL). Then, 2,2,2-trifluoro-N-(5-trimethylsilanyl-pent-2-en-4-ynyl)-acetamide (3.209 g, 12.87 mmol), dichlorobis(triphenylphosphine)palladium (0.328 g, 0.467 mmol), and Huenigs base (12 mL, 69 mmol) are added. The mixture is heated at reflux for 3 hours, after which TLC shows complete consumption of the starting pyrimidine. The mixture is concentrated under reduced pressure and purified using flash column chromatography to yield the product as an off-white solid.

Figure 11:
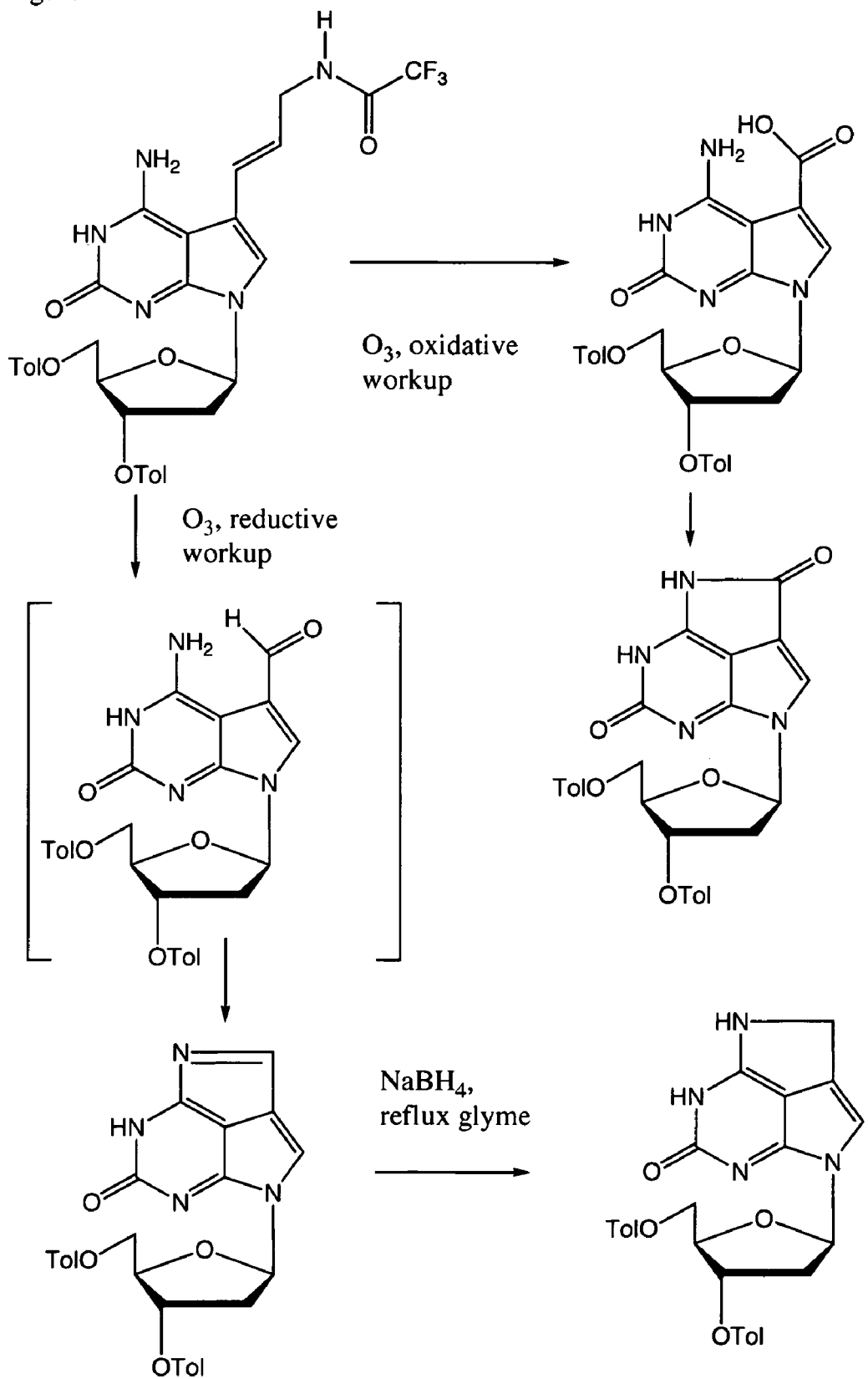
FIG. 11. The route for the synthesis of different implementations of the pu-DDA hydrogen bonding pattern, which forms a nucleobase pair with the carbocyclic pyrimidine shown in FIG. 12.

This product is treated with ozone, followed by oxidative workup and treatment with dicyclohexylcarbodiimide in tetrahydrofuran generates the cyclic lactone (FIG. 11). Treatment of this product with ozone, followed by reductive workup with dimethylsulfide, generates the cyclic imine. This is reduced by treating with 5 fold excess sodium borohydride in refluxing glyme.

Figure 12:
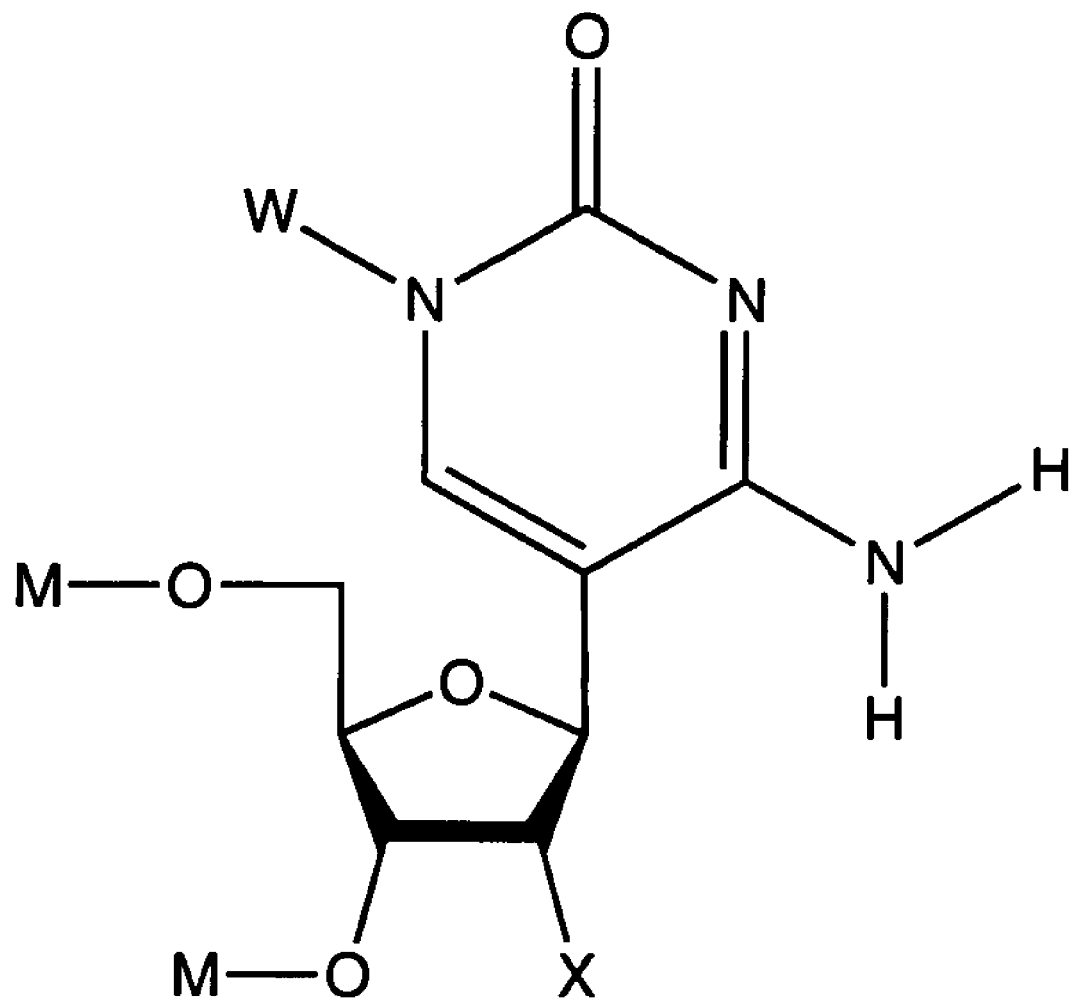
FIG. 12. A carbocyclic analog of isocytidine that is complementary to both puDDDA and puADDA implementations, as well as the structures in FIG. 11.
Figure 13:
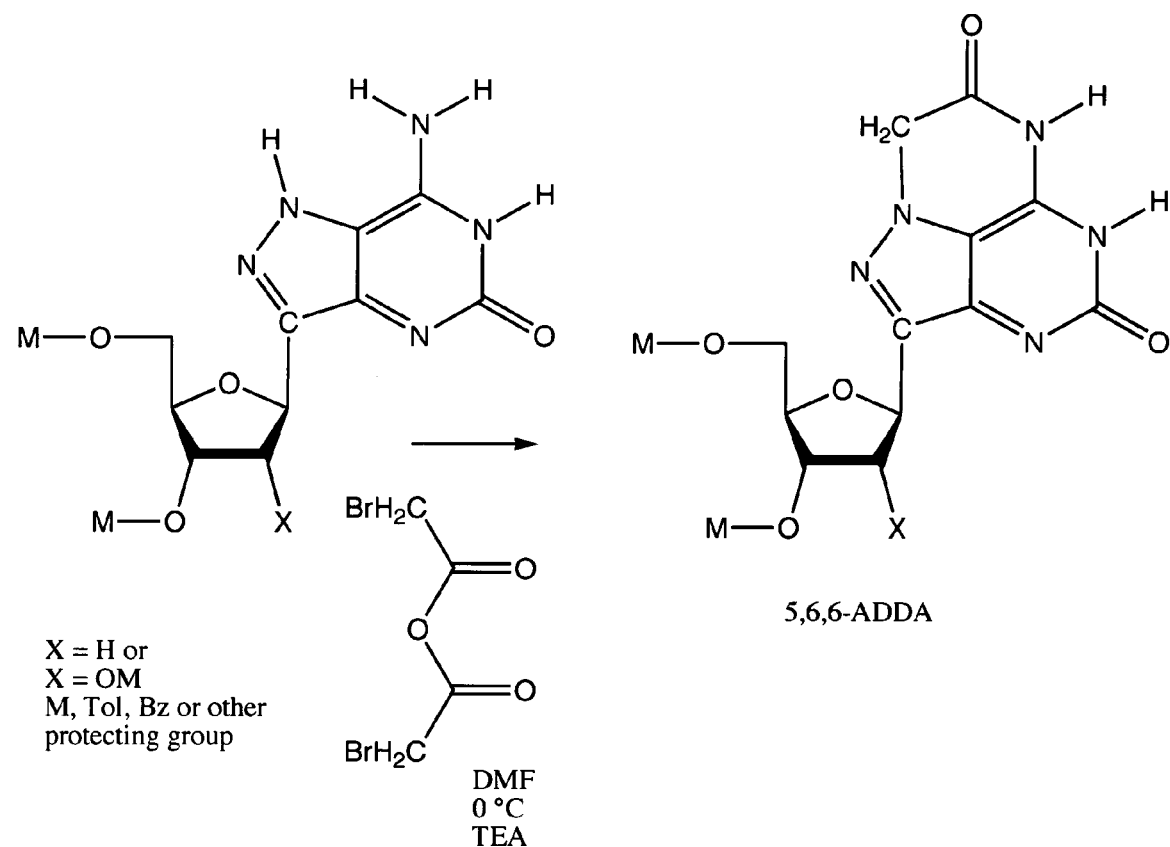
FIG. 13. Another implementation of the puADDA hydrogen bonding pattern, starting from the formycin derivative.
Figure 14:
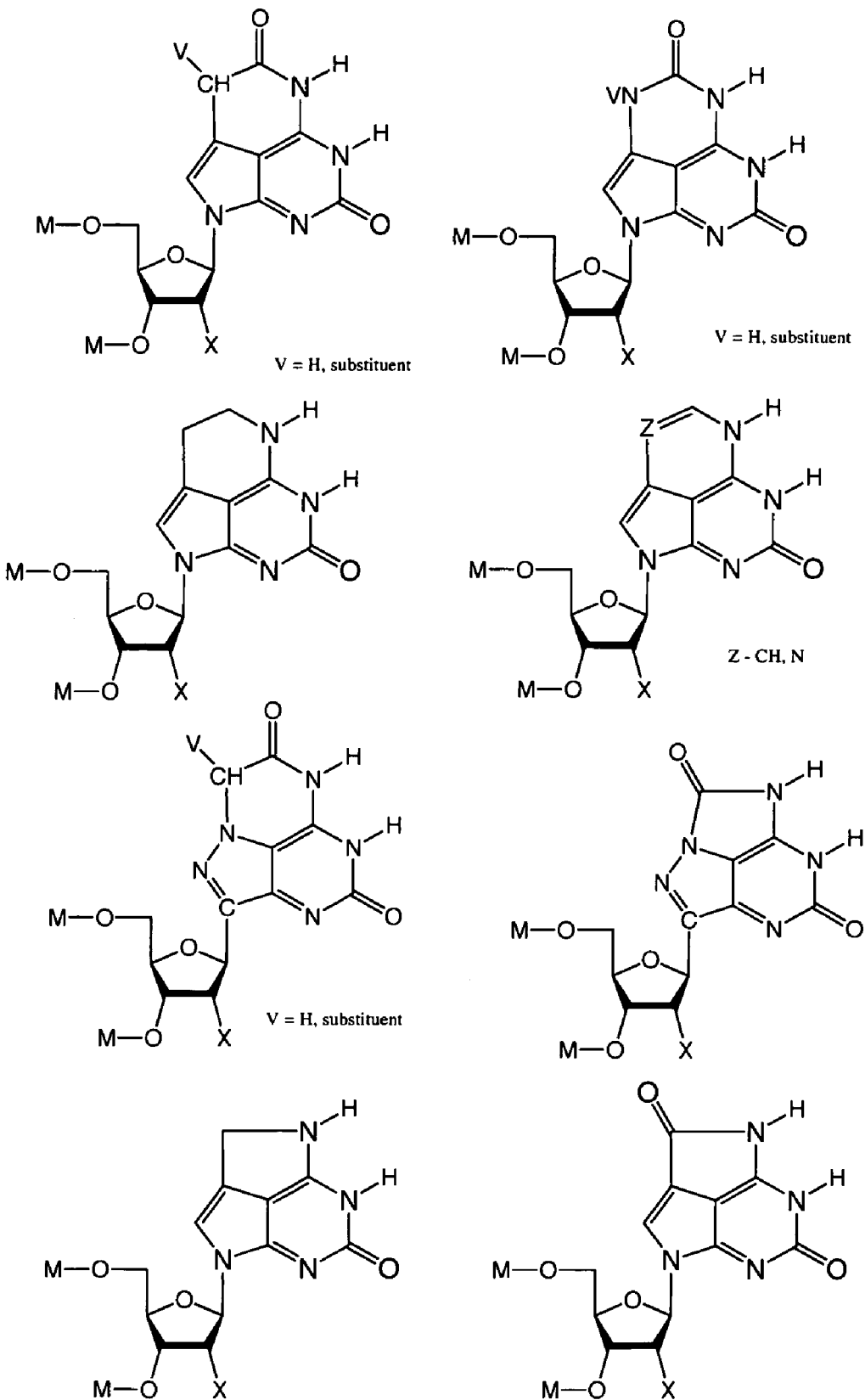
FIG. 14. Implementations of puADDA and pu-DDA patterns.

These two species generate a molecule that forms a hydrogen bond with the species shown in FIG. 12.

Example 2

Implementation of puADDA

A suspension of palladium acetate (56 mg; 0.25 mmol) and triphenylarsine (153 mg; 0.50 mmol) in DMF (7 mL) is stirred at room temperature for 30 min, resulting in a yellow suspension. A solution of the 5-iodo-2-methoxy-pyrimidine-4,6-diamine (2.5 mmol) attached to 3',5'-ditoluoyl-2'-deoxyribose and trimethylsilylacetylene (3.0 mmol) in DMF (8 mL), previously dried overnight over molecular sieves (3 Å), is added to the catalyst suspension, together with triethylamine (490 µL; 3.5 mmol) (using separate syringes). The suspension is stirred at 60° C. for 6 days. The solvents are then removed under high vacuum. The residue is suspended in $CH_2Cl_2$ (50 mL), the insoluble material removed by centrifugation and the organic solution evaporated. Column chromatography on silica using 3-8% $MeOH/CH_2Cl_2$ as eluent gave the trimethylsilylacetylene derivative.

The trimethylsilylacetylene is converted to the corresponding carboxylic acid following a procedure by Pelter et al. [Pel92]. A solution of dimesitylborane (2.5 g, 10 mmol) in THF (10 mL) is cooled on an ice bath. To the solution is added slowly, with stirring, the trimethylsilylacetylene derivative (1 mmol, in 25 mL of THF). Stirring was continued for 1 hour. The mixture is then added slowly at 0° C. to a an aqueous solution (40 mL) of sodium acetate (5 M) and hydrogen peroxide (9.6 mL). The mixture is stirred for 2 hours, and then allowed to warm to room temperature. The byproduct (2,4,6-trimethylphenol) was removed by extraction with ether, the aqueous layer was acidified, and the resulting heterocycle-acetic acid is purified by chromatography on silica gel.

The ring is then closed by dissolving the product in tetrahydrofuran that had been dried over molecular sieves, together with 1.1 equivalents of dicyclohexylcarbodiimide (DCC).

The same compound can be prepared by Heck coupling with the $Me_3Si$—CC—$CH_2COOR$ unit, which is known in the art [Lepore, S. D.; He, Y.; Damisse, P. Studies on the Base-Promoted Conversion of Conjugated Alkynyl Esters to α-Substituted α-Allenyl Esters. *J. Org. Chem.* (2004), 69(26), 9171-9175][Davies, H. M. L.; Boebel, T. A. Asymmetric synthesis of 1-alkynylcyclopropane-1-carboxylates. *Tetrahedron Letters* (2000), 41(43), 8189-819].

These may also be prepared from the 7-halo-7-deazaisoguanosine derivatives, or their 2'-deoxy analogs, as known in the art [Li, H., Peng, X., Seela, F. (2004) Fluorescence quenching of parallel-stranded DNA bound ethidium bromide: the effect of 7-deaza-2'-deoxyisoguanosine and 7-halogenated derivatives. *Bioorganic & Medicinal Chemistry Letters* 14(24), 6031-6034][Seela, F., Peng, X. (2004) Regioselective syntheses of 7-halogenated 7-deazapurine nucleosides related to 2-amino-7-deaza-2'-deoxyadenosine and 7-deaza-2'-deoxyisoguanosine. *Synthesis*, 1203-1210].

Example 3

Formycin Analogs Implementing the puADDA Hydrogen Bonding Pattern

The formycin analog of isoguanosine has been reported as the riboside, and as the dihydroxypropyl derivative. The riboside prepared as the 2'-deoxyriboside either by Barton deoxygenation of the appropriately protected riboside or by direct ring annelation of the nitrocyanopyrazole [Reich, N. O., Allan, B. W., Lindstrom, W. M., Putzke, A. P. (2002) Fluorescence assay for DNA modifying enzymes. U.S. Pat. Appl. Publ., 6 pp. US 2002127593] [Robertus, J. (1998) Ricin inhibitors for control of nonspecific cytotoxicity. PCT Int. Appl., 72 pp. WO 9828298][Bzowska, A., Kulikowska, E., Shugar, D. (1992) Formycins A and B and some analogs: Selective inhibitors of bacterial (*Escherichia coli*) purine nucleoside phosphorylase. *Biochim. Biophys. Acta* 1120, 23947][Buchanan, J. G, Harrison, M, Wightman, R. H., Harnden, M. R. (1989) C-nucleoside studies. Part 20. Synthesis of some pyrazolo[4,3-d]pyrimidine acyclonucleosides related to (S)-(2,3-dihydroxypropyl)adenine. A direct method for double functionalization of the pyrazole ring. *J.*

*Chem. Soc., Perkin Trans.* 1925-30][Ghose, A. K., Crippen, G. M., Revankar, G. R., McKernan, P. A., Smee, D. F., Robins, R. K. (1989) Analysis of the in vitro antiviral activity of certain ribonucleosides against parainfluenza virus using a novel computer aided receptor modeling procedure. *J. Med. Chem.* 32, 746-756][Ugarkar, B. G.; Revankar, G. R.; Robins, R. K. (1984) A simple oxidation of formycin to oxoformycin and oxoformycin B. Synthesis of 6-methyloxoformycin, a C-nucleoside analog of doridosine. *J. Heterocyclic Chem.* 21, 1865-70][Bose, S, N., Kumar, S., Davies, J. H., Sethi, S. K., McCloskey, J. A. (1984) Conversion of formycin into the fluorescent isoguanosine analog 7-amino-3-(β-D-ribofuranosyl)-1H-pyrazolo[4,3-d]pyrimidin-5(4H)-one. *J. Chem. Soc., Perkin Transactions* 1, 2421-3]. The formycin analog of isoguanosine is dissolved in anhydrous tetrahydrofuran, treated with 1.1 equiv. NaH, and with 1.1 equivalents of ethylbromoacetate. The product closes spontaneously to give the puADDA product.

Example 4

Making Phosphoramidites of the Appropriately Protected Derivative of the 2'-Deoxyribonucleoside Analog Suitable for DNA Synthesis As is standard in the field, the exocyclic amino groups are protected as phenoxyacetylamides. Tritylation.

The protected 2'-deoxyribonucleoside analog (8.7 mmol) is dissolved in dry pyridine (150 mL). To the solution is added 4',4"-dimethoxytrityl chloride (1.2 equiv). The reaction mixture is stirred at room temperature for 24 hours. The reaction is quenched by the addition of water (3 mL). The solution is concentrated under vacuum, and an aqueous solution of NaHCO$_3$ (80 mL) is added. The mixture is extracted with EtOAc, dried (Na$_2$SO$_4$), the solvents evaporated under reduced pressure, and the product isolated by column chromatography (chloroform/acetone 9:1, then 9:2).

Phosphoramidite Synthesis

The protected derivative from above (0.12 mmol) is dissolved in CH$_3$CN (2.0 mL). The solution is then treated with bis-(N,N-diisopropylamino)-3-cyanoethyloxyphosphine (Aldrich, 1.2 equiv.), and diisopropylammonium tetrazolide (0.06 mmol), following a literature procedure [McBride, L. J., Kierzek, R., Beaucage, S. L. & Caruthers, M. H. (1986) *J. Am. Chem. Soc.* 108, 2040-2048]. The progress of the reaction was monitored by TLC (SiO$_2$ eluted with EtOAc:CH$_2$Cl$_2$: triethylamine 45:45:10). An additional portion (0.02 mL) of bis-(N,N-diisopropylamino)-3-cyanoethyloxyphosphine was then added, and stirring continued for an additional hour. Water (2 drops) was added, the mixture stirred for 15 min, the mixture diluted with CH$_2$Cl$_2$ (30 mL), and the organic layer washed with aqueous Na$_2$CO$_3$ (2%) and dried (Na$_2$SO$_4$). The phosphoramidite (120.3 mg, 93%) was isolated by chromatography (SiO$_2$, EtOAc:CH$_2$Cl$_2$:triethylamine 45:45:10 as eluant). $^{31}$P-NMR 149.7 (doublet of diastereomers).

Example 5

Chemical Synthesis of Oligonucleotide Analogs Incorporating the Disclosed Nucleoside Analog Oligonucleotide analogs containing non-standard nucleotide are prepared by "trityl off" solid-phase synthesis using an Applied Biosystems automated DNA synthesizer from the β-cyanoethyl protected phosphoramidites. They are purified by polyacrylamide gel electrophoresis (12-20%). Chemicals are from Glen Research, while the DNA membrane columns (0.2 μmol scale) and CPG columns (1.0 μmol scale) containing the 3'-terminal nucleoside are from PerSeptive Biosystems.

Vials to contain the protected phosphoramidite of the nucleoside analog are rinsed with acetone and immediately placed into an oven at 150° C. to dry overnight. The vials are then cooled to room temperature in a dessicator over P$_2$O$_5$ under vacuum of <1 torr. The dessicator is vented with dry Ar, and phosphoramidite is placed into the vials. If only a small amount of phosphoramidite is available, the compound is transferred into the prepared vial as solution in CH$_2$Cl$_2$, and the solvent is evaporated under reduced pressure. Subsequently, the vials containing the phosphoramidites are returned to the desiccator with P$_2$O$_5$ to be stored under vacuum. The desiccator is vented with dry Ar, and the vials are immediately closed and stored in a dessicator containing anhydrous MgSO$_4$ until needed.

Directly before oligonucleotide synthesis, the phosphoramidites are dissolved in anhydrous acetonitrile (0.15 g/1.5 mL). Standard phosphoramidites are used as solutions in anhydrous acetonitrile (0.5 g/10 mL) at half the concentration that is recommended by the synthesizer manufacturer. Synthesis on a 0.2-1.0 μmol scale is performed using a standard synthesis protocol, with the exception of an extended coupling time (600 s) for the analog.

After the synthesis is complete (0.2-1.0 μmol scale), the column material (CPG beads) is transferred into a 1.5 mL microcentrifuge tube with sealed screw cap. Upon addition of conc. NH$_4$OH solution (1 mL), the tube is shaken in an Eppendorf shaker at maximum speed overnight at 55° C. After the mixture had been centrifuged for a few seconds, the supernatant is transferred into a clean microfuge tube. The column material is washed with water (250 μL), and the supernatant is combined with the first supernatant. The solvent is evaporated from the combined supernatants by means of a speed vac at ambient temperature. The residue is dissolved in NaOAc solution (0.7 M, pH 5.2; 300 μL). Any cloudy precipitate is removed by filtration through a syringe filter with cellulose acetate membrane (pore size 0.2 μm). Ice cold EtOH (1 mL) is added to the clear solution. After vortexing, the mixture is stored at −20° C. for several hours. The mixture is then centrifuged at 4° C. and 14,000 rpm for 30 min, and the supernatant is removed. The remaining pellet is washed with 80% aqueous EtOH (1 mL) by gentle shaking, and the mixture is centrifuged again at 4° C. and 14,000 rpm for 10 min. After removal of the supernatant, the oligonucleotide pellet is dried by exposure to the air and redissolved in water (500 μL).

The oligonucleotide analog is purified by either HPLC that is obtained after above described post synthetic processing is mixed with PAGE loading buffer (1:1). The mixture is incubated at 95° C. for 2 min and immediately loaded onto the preheated polyacrylamide gel. Up to ¼ of a 0.2 μmol synthesis or 1/20 of a 1.0 μmol synthesis is loaded into one well. Electrophoresis is performed at 45-55 W, maintaining a gel temperature of 55-60° C. When the desired oligonucleotides had migrated ca. 25 cm as judged by the dye markers, electrophoresis is stopped. The oligonucleotide bands are visualized by UV quenching with the help of a silica gel coated TLC plate containing a fluorescence indicator. The desired bands are cut out with a razor blade. Usually the slowest migrating band of a crude mixture corresponded to the desired full length product. The gel pieces are transferred into tubes of appropriate size and crushed with the help of a pipette tip. NaOAc solution (300 mM, pH 7.5) is added to completely cover the gel particles. The mixture is shaken vehemently on a vortexer for 5 h to overnight. After centrifugation, the supernatant is removed. The gel particles are shaken with a fresh portion of NaOAc solution (300 mM, pH 7.5) for a few hours. The supernatant is filtered and combined with the supernatant from the first extraction. The combined supernatants are filtered through a cellulose acetate membrane (pore size 0.2 µm). The oligonucleotide is recovered from the filtrate by EtOH precipitation. The pellet is washed with 70% EtOH. The so obtained oligonucleotides are pure enough for all-subsequent applications. They are stored as solutions in water (3-250 µmol/µL) at −20° C.

The concentrations of the oligonucleotide solutions are determined via measurement of the UV absorbance of the oligonucleotide solution at λ=260 nm.

The relation between UV absorbance and the amount of the oligonucleotide (in nanomoles) present in the sample is given approximately by the formula $A_{260}*100/n$=nmole oligonucleotide, where $A_{260}$ is the absorbance at λ=260 nm in OD, and n is the number of bases of the oligonucleotide. This formula is employed for both standard and functionalized oligonucleotides without consideration of the extinction coefficient of the functionalized bases.

Oligonucleotide analogs are analyzed by anion exchange HPLC under the following conditions:

Column: Dionex

Solvent A: Sodium phosphate (20 mM, pH 6.0); solvent B: Sodium phosphate (20 mM, pH 6.0), NaCl (1 M); solvent C: ACN.

Gradient: 0-1 min 75% A/25% C; 30 min 55% B/25% C (linear).

For purification of large amounts of oligonucleotides (up to 10 OD), a larger column with the same packing material is used. The gradients are adjusted to keep the Rt value about constant. On the preparative scale, the oligonucleotides are further purified and desalted on a larger column (Nova-Pak HR C18 cartridge (Waters), 60 Å, 25×100 mm; flow rate 5.5 mL/min).

Oligonucleotide analogs containing the nucleotide analog are characterized by MALDI-TOF mass spectrometry. Short oligonucleotides (9-10mers) are in addition analyzed by electrospray ionization mass spectrometry (ESI MS). The oligonucleotide is injected as solution in isopropanol/water (1:1) containing TEA (30 mM).

The oligonucleotide analogs can be further analyzed by enzymatic degradation. The analog is dissolved in water/acetonitrile mixtures (9:1, 4.0 µL). Digestion buffer (0.1 M Tris-HCl, pH 8.3, 20 mM $MgCl_2$; 4.0 µL) and 10 mM $Zn(OAc)_2$ solution (1.0 µL) is then added, followed by phosphodiesterase I (1.0 µL, 0.0006 U), nuclease P1 (1 µL, 0.0006 U) and alkaline phosphatase, diluted with digestion buffer (1.0 µL, 1.5 U). The mixture is incubated at 50° C. for 5 h. The sample is then diluted with triethylammonium acetate buffer (1 M, pH 7.0, 20 µL) and water/acetonitrile (9:1, 70 µL), filtered and analyzed using RP-HPLC (Column: Adsorbosphere, Solvent A: TEAOAc (25 mM, pH 7.0); solvent B: acetonitrile 4:1; solvent C: acetonitrile. The composition of the oligonucleotide is verified by using the integrated absorbance of the component nucleosides at 260 nm.

What is claimed is:

1. A pair of complementary oligonucleotides strands bonded in a duplex by at least one nucleobase pair that is represented by a structure selected from the group consisting of

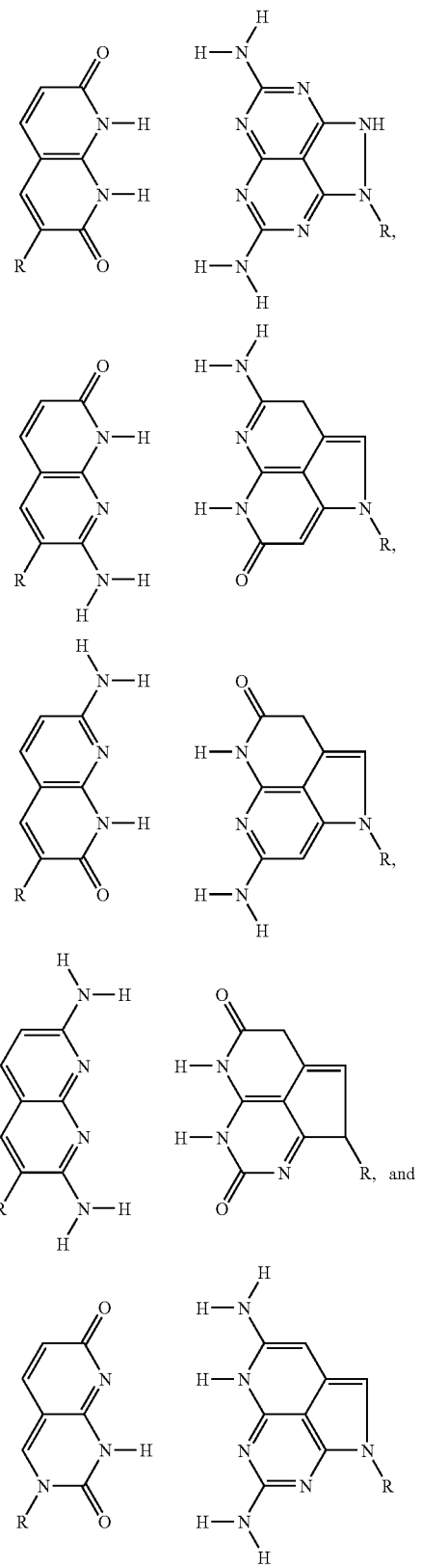

wherein R represents the point of attachment to a ribose or 2'-deoxyribose ring.

2. A pair of complimentary oligonucleotide strands bonded in a duplex by at least one nucleobase pair, wherein one component of said nucleobase pair is selected from the group consisting of
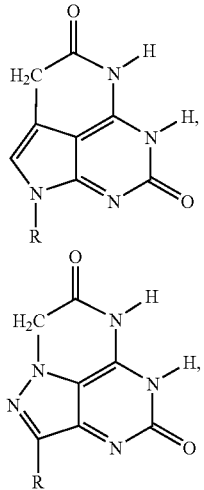
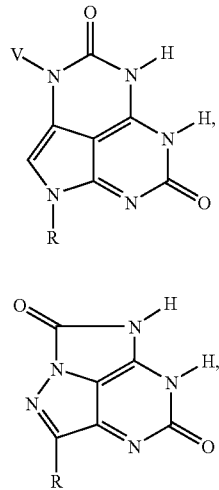
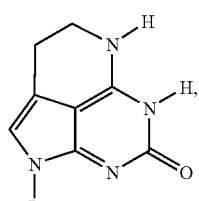
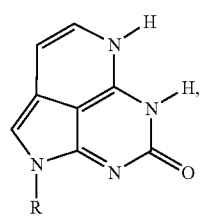
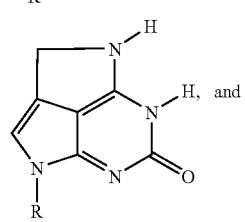
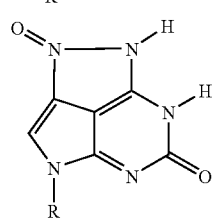
wherein V is a hydrogen and R represents the point of attachment to a ribose or 2'-deoxyribose ring.
* * * * *